US008394764B2

(12) United States Patent
Boyd et al.

(10) Patent No.: US 8,394,764 B2
(45) Date of Patent: Mar. 12, 2013

(54) GRIFFITHSIN, GLYCOSYLATION-RESISTANT GRIFFITHSIN, AND RELATED CONJUGATES, COMPOSITIONS, NUCLEIC ACIDS, VECTORS, HOST CELLS, METHODS OF PRODUCTION AND METHODS OF USE

(75) Inventors: Michael R. Boyd, Mobile, AL (US); Toshiyuki Mori, San Francsico, CA (US); Barry R. O'Keefe, Frederick, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/022,289

(22) Filed: Feb. 7, 2011

(65) Prior Publication Data

US 2011/0189105 A1    Aug. 4, 2011

Related U.S. Application Data

(62) Division of application No. 11/569,813, filed as application No. PCT/US2005/018778 on May 27, 2005, now Pat. No. 7,884,178.

(60) Provisional application No. 60/576,056, filed on Jun. 1, 2004.

(51) Int. Cl.
*A61K 38/00* (2006.01)
*A01N 37/18* (2006.01)
*A61P 31/00* (2006.01)
*A61P 31/18* (2006.01)
*A61P 31/22* (2006.01)
*A61P 1/16* (2006.01)

(52) U.S. Cl. ............. 514/3.7; 514/1.1; 514/2.3; 514/3.8; 514/4.2; 514/4.3

(58) Field of Classification Search ......................... None
See application file for complete search history.

(56) References Cited

U.S. PATENT DOCUMENTS 7,314,974 B2    1/2008 Cao et al.

OTHER PUBLICATIONS

Gait et al. Progress in anti-HIV structure-based drug design. Trends in Biotechnology Oct. 1995, vol. 13, No. 10, p. 430-438.*
Yin et al. Overcoming HIV drug resistance through rational drug design based on molecular, biochemical, and structural profiles of HIV resistance. Cellular and Molecular Life Sciences Aug. 2006, vol. 63(15), p. 1706-1724.*
Shepard et al. A Single Amino Acid Change in IFN-betal abolishes its antiviral activity. Nature 1981, vol. 294, pp. 563-565.*
Meyerhans et al. Temporal Fluctuations in HIV Quasispecies In Vivo are Not Reflected by Sequential HIV Isolations. Cell 1989, vol. 58, pp. 901-910.*
Kusumi et al. Human Immunodeficiency Virus Type 1 Envelope Gene Structure and Diversity In Vivo and after Cocultivation In Vitro. Journal of Virology, 1992, vol. 66, No. 2, p. 875-885.*
Jones et al. Inhibition of Influenza Virus Infection by a Novel Antiviral Peptide That Targets Viral Attachment to Cells. Journal of Virology 2006, vol. 80, No. 24, p. 11960-11967.*
Hendrix et al. Pharmacokinetics and Safety of AMD-3100. Antimicrobial Agents and Chemotherapy, Jun. 2000, vol. 44, No. 6, p. 1667-1673.*
Coffin, "HIV population dynamics in vivo: implications for genetic variation, pathogenesis, and therapy," *Science*, 267 (5197), 483-489 (1995).
Cohen, "High turnover of HIV in blood revealed by new studies," *Science*, 267 (5195), 179 (1995).
De Clercq, "Basic Approaches to Anti-Retroviral Treatment," *J. Acquir. Immun. Def. Synd.*, 4, 207-218 (1991).
De Clercq, "Antiviral Agents: Characteristic Activity Spectrum Depending on the Molecular Target with which they Interact," *Adv. Virus Res.*, 42, 1-55 (1993).
Jones et al., "Inhibition of influenza virus infection by a novel antiviral peptide that targets viral attachment to cells," *J. Virol.*, 80 (24), 11960-11967 (2006).
Kaneko et al., "Complete genomic sequence of the filamentous nitrogen-fixing cyanobacterium *Anabaena* sp. strain PCC 7120" *DNA Res.*, 8 (5), 205-213 (2001).
Lee et al., EBI Abstract: Putative 32.7kDa jasmonate-induced protein (32 kDa protein), Accession No. 040007 (Nov. 1, 1996 integrated into UniProtKB/TrEMBL).
Mitsuya et al., "Molecular targets for AIDS therapy," *Science*, 249 (4976), 1533-1544 (1990).
Mori et al., "Isolation and characterization of griffithsin, a novel HIV-inactivating protein, from the red alga *Griffithsia* spb," *J. Biol. Chem.*, 280 (10), 9345-9353 (2005).
Shepard et al., "A single amino acid change in IFN-beta1 abolishes its antiviral activity," *Nature*, 294 (5841), 563-565 (1981).
Tsai et al., "Cyanovirin-N gel as a topical microbicide prevents rectal transmission of SHIV89.6P in macaques," *AIDS Res. Hum. Retroviruses*, 19 (7), 535-541 (2003).

(Continued)

*Primary Examiner* — Louise Humphrey
(74) *Attorney, Agent, or Firm* — Leydig, Voit & Mayer, Ltd.

(57) ABSTRACT

An isolated and purified nucleic acid molecule that encodes a polypeptide comprising at least eight contiguous amino acids of SEQ ID NO: 3, wherein the at least eight contiguous amino acids have anti-viral activity, as well as an isolated and purified nucleic acid molecule that encodes a polypeptide comprising at least eight contiguous amino acids of SEQ ID NO: 3, wherein the at least eight contiguous amino acids have anti-viral activity, and, when the at least eight contiguous amino acids comprise amino acids 1-121 of SEQ ID NO: 3, the at least eight contiguous amino acids have been rendered glycosylation-resistant, a vector comprising such an isolated and purified nucleic acid molecule, a host cell comprising the nucleic acid molecule, optionally in the form of a vector, a method of producing an anti-viral polypeptide or conjugate thereof, the anti-viral polypeptide itself, a conjugate or fusion protein comprising the anti-viral polypeptide, and compositions comprising an effective amount of the anti-viral polypeptide or conjugate or fusion protein thereof. Further provided are methods of inhibiting prophylactically or therapeutically a viral infection of a host.

21 Claims, 11 Drawing Sheets

OTHER PUBLICATIONS

Figure 1:
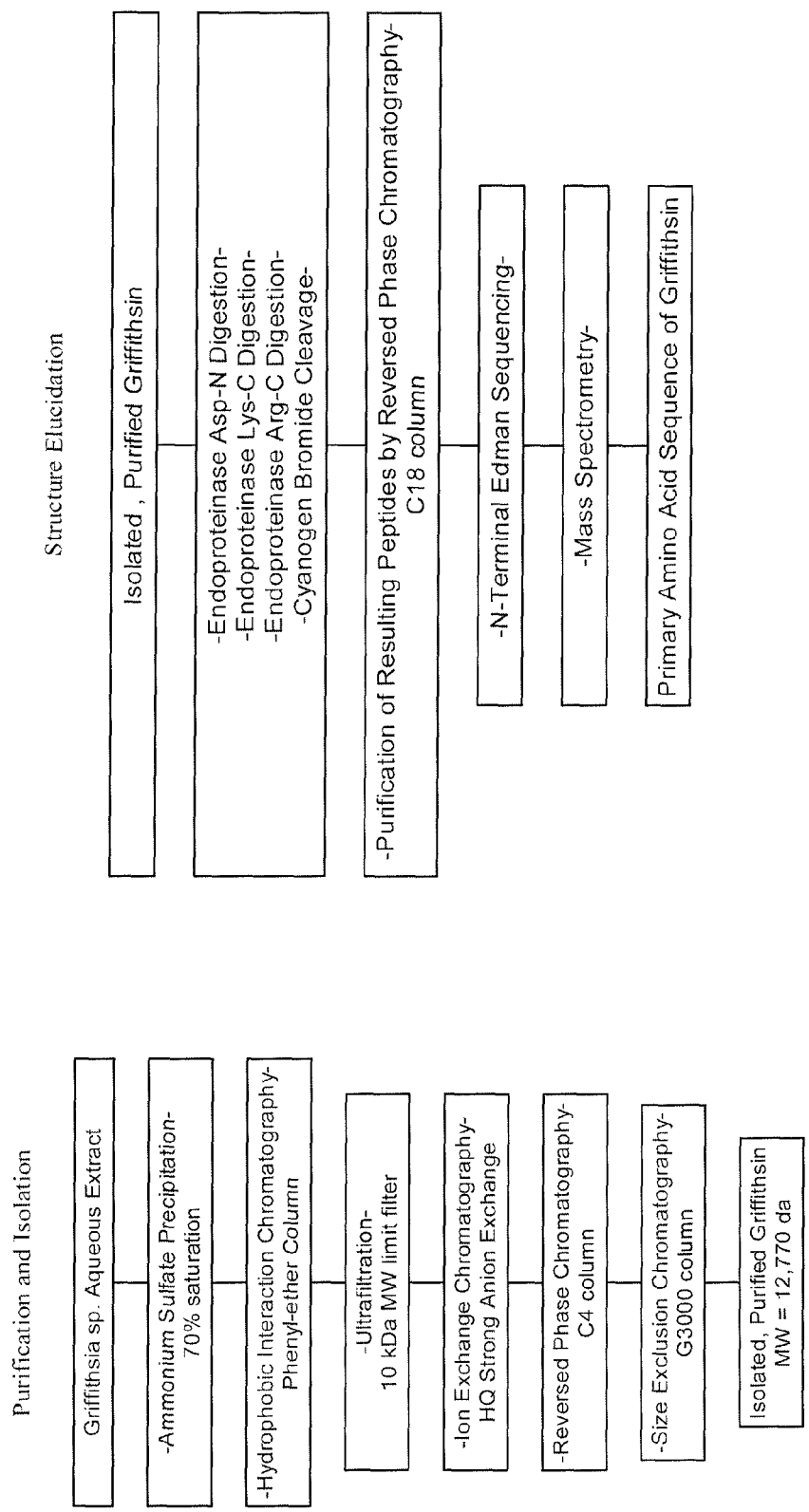

Tsai et al., "Cyanovirin-N inhibits AIDS virus infections in vaginal transmission models," *AIDS Res. Hum. Retroviruses*, 20 (1), 11-18 (2004).

Lee et al., "Jasmonate signalling can be uncoupled from abscisic acid signalling in barley: identification of jasmonate-regulated transcripts which are not induced by abscisic acid," *Planta*, 199 (4), 625-632 (1996).

Wohlford-Lenane et al. "Protective role of griffithsin in severe acute respiratory syndrome pulmonary infection," *Am. J. Respir. Crit. Care Med.*, 179: A5954 (2009).

Japanese Patent Office, First Office Action in Japanese Patent Application No. 2007-515398 (Jan. 11, 2011).

\* cited by examiner

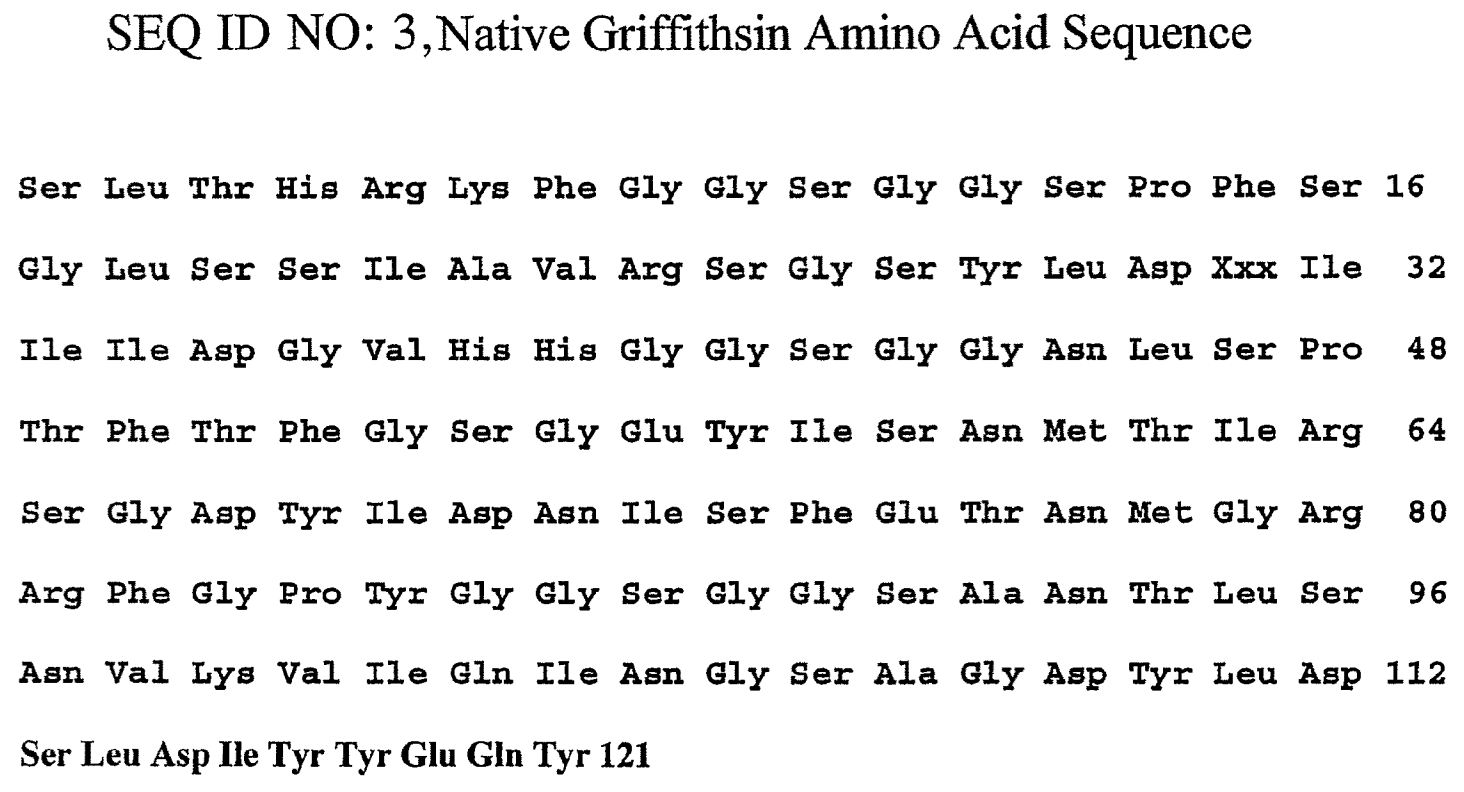

SEQ ID NO: 3, Native Griffithsin Amino Acid Sequence

```
Ser Leu Thr His Arg Lys Phe Gly Gly

SEQ ID NO: 1, DNA Sequence Encoding Native Griffithsin Polypeptide

```
AGC CTG ACC CAT CGC A

SEQ ID NO: 2, Recombinant Griffithsin Amino Acid Sequence

```
Ser Leu Thr His Arg Lys Phe Gly Gly Ser Gly Gly Ser Pro Phe Ser   16
Gly Leu Ser Ser Ile Ala Val Arg Ser Gly Ser Tyr Leu Asp Ala Ile   32
Ile Ile Asp Gly Val His His Gly Gly Ser Gly Gly Asn Leu Ser Pro   48
Thr Phe Thr Phe Gly Ser Gly Glu Tyr Ile Ser Asn Met Thr Ile Arg   64
Ser Gly Asp Tyr Ile Asp Asn Ile Ser Phe Glu Thr Asn Met Gly Arg   80
Arg Phe Gly Pro Tyr Gly Gly Ser Gly Gly Ser Ala Asn Thr Leu Ser   96
Asn Val Lys Val Ile Gln Ile Asn Gly Ser Ala Gly Asp Tyr Leu Asp  112
Ser Leu Asp Ile Tyr Tyr Glu Gln Tyr 121
```

Figure 9

SEQ ID NO: 4, DNA Sequence Encoding Recombinant His-tagged Griffithsin

```
ATG GGC AGC AGC CAT CAT CAT

SEQ ID NO: 5, Recombinant His-Tagged Griffithsin Amino Acid Sequence

```
Met Gly Ser Ser His His His His His His Ser Ser Gly Leu Val Pro  16
Arg Gly Ser Leu Thr His Arg Lys Phe Gly Gly Ser Gly Gly Ser Pro  32
Phe Ser Gly Leu Ser Ser Ile Ala Val Arg Ser Gly Ser Tyr Leu Asp  48
Ala Ile Ile Ile Asp Gly Val His His Gly Gly Ser Gly Gly Asn Leu  64
Ser Pro Thr Phe Thr Phe Gly Ser Gly Glu Tyr Ile Ser Asn Met Thr  80
Ile Arg Ser Gly Asp Tyr Ile Asp Asn Ile Ser Phe Glu Thr Asn Met  96
Gly Arg Arg Phe Gly Pro Tyr Gly Gly Ser Gly Gly Ser Ala Asn Thr 112
Leu Ser Asn Val Lys Val Ile Gln Ile Asn Gly Ser Ala Gly Asp Tyr 128
Leu Asp Ser Leu Asp Ile Tyr Tyr Glu Gln Tyr 139
```

Figure 11

GRIFFITHSIN, GLYCOSYLATION-RESISTANT GRIFFITHSIN, AND RELATED CONJUGATES, COMPOSITIONS, NUCLEIC ACIDS, VECTORS, HOST CELLS, METHODS OF PRODUCTION AND METHODS OF USE

CROSS-REFERENCE TO RELATED APPLICATIONS

This patent application is a divisional of U.S. patent application Ser. No. 11/569,813, filed Dec. 12, 2006, which issued as U.S. Pat. No. 7,884,178, which is the U.S. national phase of PCT/US05/18778, filed on May 27, 2005, which claims the benefit of U.S. Provisional Patent Application No. 60/576,056, filed Jun. 1, 2004, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,345 Byte ASCII (Text) file named "707632ST25.TXT," created on Feb. 3, 2011.

Applicants respectfully request entry into the specification of the Sequence listing submitted herewith.

TECHNICAL FIELD OF THE INVENTION

The invention relates to an anti-viral polypeptide, a glycosylation-resistant anti-viral polypeptide, and related conjugates, compositions, nucleic acids, vectors, host cells, antibodies and methods of production and use.

BACKGROUND OF THE INVENTION

The field of viral therapeutics has developed in response to the need for agents effective against retroviruses, especially HIV. There are many ways in which an agent can exhibit anti-retroviral activity (e.g., see DeClercq, *Adv. Virus Res.*, 42: 1-55 (1993); DeClercq, *J. Acquir. Immun. Def. Synd.*, 4: 207-218 (1991); and Mitsuya et al., *Science*, 249: 1533-1544 (1990). Nucleoside derivatives, such as AZT, which inhibit the viral reverse transcriptase, were among the first clinically active agents available commercially for anti-HIV therapy. Although very useful in some patients, the utility of AZT and related compounds is limited by toxicity and insufficient therapeutic indices for fully adequate therapy. Also, given the subsequent revelations about the true dynamics of HIV infection (Coffin, *Science*, 267: 483-489 (1995); and Cohen, *Science*, 267: 179 (1995)), it has become increasingly apparent that agents acting as early as possible in the viral replicative cycle are needed to inhibit infection of newly produced, uninfected immune cells generated in the body in response to the virus-induced killing of infected cells. Also, it is essential to neutralize or inhibit new infectious virus produced by infected cells.

Effective means for preventing HIV infection also are needed as a global priority. Heterosexual transmission accounts for the majority of new cases of HIV infection each year. Current reports from the World Health Organization estimate that a total of more than 40 million people are now infected with HIV. HIV prevention research has to date focused predominantly on vaccine development. However, no effective preventative or therapeutic vaccine has been identified thus far. New approaches to vaccine development, as well as entirely different strategies and agents for preventing person-to-person transmission of HIV infection, are needed. One approach showing great promise is the development and use of topical microbicides. In this approach, a suitable antiviral agent is applied directly at the potential site of virus exposure, e.g., the genital mucosa in the case of HIV. A suitable antiviral agent is one which inactivates or inhibits infectivity of a virus upon contact of the antiviral agent with the virus. Suitable animal models are available for demonstrating in vivo efficacy of such approaches for preventing transmission of immunodeficiency viruses, such as HIV. For instance, the HIV-inactivating protein, cyanovirin-N, has been shown to inhibit the sexual transmission of a chimeric simian/human immunodeficiency virus (SHIV) infection in a primate model employing macaques exposed to the virus vaginally or rectally (C-C Tsai et al., *AIDS Res. Hum. Retroviruses*, 19, 535-541 (2003) and C-C Tsai et al., *AIDS Res. Hum. Retroviruses*, 20, 11-18 (2004)).

Infection of people by influenza viruses is also a major cause of pandemic illness, morbidity and mortality worldwide. The adverse economic consequences, as well as human suffering, are enormous. Available treatments for established infection by this virus are either minimally effective or ineffective; these treatments employ amantatadine, rimantadine and neuraminidase inhibitors. Of these drugs, only the neuraminidase inhibitors are substantially active against multiple strains of influenza virus that commonly infect humans, yet these drugs still have limited utility or efficacy against pandemic disease.

Currently, the only effective preventative treatment against influenza viral infection is vaccination. However, this, like the drug treatments, is severely limited by the propensity of influenza viruses to mutate rapidly by genetic exchange, resulting in the emergence of highly resistant viral strains that rapidly infect and spread throughout susceptible populations. In fact, a vaccination strategy is only effective from year-to-year if the potential pandemic strains can be identified or predicted, and corresponding vaccines prepared and administered early enough that the year's potential pandemic can be aborted or attenuated. Thus, new preventative and therapeutic interventions and agents are urgently needed to combat influenza viruses.

New agents with broad anti-influenza virus activity against diverse strains, clinical isolates and subtypes of influenza virus would be highly useful, since such agents would most likely remain active against the mutating virus. The two major types of influenza virus that infect humans are influenza A and B, both of which cause severe acute illness that may include both respiratory and gastrointestinal distress, as well as other serious pathological sequellae. An agent that has anti-influenza virus activity against diverse strains and isolates of both influenza A and B, including recent clinical isolates thereof, would be particularly advantageous for use in prevention or treatment of hosts susceptible to influenza virus infection.

The predominant mode of transmission of influenza viral infection is respiratory, i.e., transmission via inhalation of virus-laden aerosolized particles generated through coughing, sneezing, breathing, etc., of an influenza-infected individual. Transmission of infectious influenza virions may also occur through contact (e.g., through inadvertent hand-to-mouth contact, kissing, touching, etc.) with saliva or other bodily secretions of an infected individual. Thus, the primary first points of contact of infectious influenza virions within a susceptible individual are the mucosal surfaces within the oropharyngeal mucosa, and the mucosal surfaces within the upper and lower respiratory tracts. Not only do these sites comprise first points of virus contact for initial infection of an individual, they are also the primary sites for production and exit (e.g., by coughing, sneezing, salivary transmission, etc.) of bodily fluids containing infectious influenza viral particles. Therefore, availability of a highly potent anti-influenza virus agent, having broad-spectrum activity against diverse strains and isolates of influenza viruses A and B, which could be applied or delivered topically to the aforementioned mucosal sites of contact and infection and transmission of infectious influenza viruses, would be highly advantageous for therapeutic and preventative inhibition of influenza viral infection, either in susceptible uninfected or infected hosts.

In this regard, new classes of anti-viral agents, to be used alone or in combination existing anti-viral agents, are needed for effective anti-viral therapy. New agents are also important for the prophylactic inhibition of viral infection. In both areas of need, the ideal new agent(s) would act as early as possible in the viral life cycle; be as virus-specific as possible (i.e., attack a molecular target specific to the virus but not the host); render the intact virus noninfectious; prevent the death or dysfunction of virus-infected cells; prevent further production of virus from infected cells; prevent spread of virus infection to uninfected cells; be highly potent and active against the broadest possible range of strains and isolates of a given virus; be resistant to degradation under physiological and rigorous environmental conditions; and be readily and inexpensively produced.

Accordingly, the invention provides a novel anti-viral polypeptide and related conjugates, nucleic acids, vectors, host cells and methods of production and use. This and other advantages of the invention, as well as additional inventive features, will become apparent from the description provided herein.

BRIEF SUMMARY OF THE INVENTION

The invention provides, among other things, an isolated and purified nucleic acid molecule that encodes a polypeptide comprising at least eight contiguous amino acids of SEQ ID NO:3, wherein the at least eight contiguous amino acids have anti-viral activity, optionally as part of an encoded fusion protein. In this regard, the invention also provides an isolated and purified nucleic acid molecule that encodes a polypeptide comprising at least eight contiguous amino acids of SEQ ID NO:3, wherein the at least eight contiguous amino acids comprise amino acids 1-121 of SEQ ID NO:3 which have been rendered glycosylation-resistant and wherein the at least eight contiguous amino acids have antiviral activity, optionally as part of an encoded fusion protein. Further provided are vectors comprising an aforementioned isolated and purified nucleic acid molecule and a host cell or organism comprising such a vector.

Accordingly, the invention also provides a method of producing an anti-viral polypeptide, which method comprises expressing the nucleic acid molecule, optionally in the form of a vector, in a host cell or organism. Thus, an anti-viral polypeptide comprising at least eight contiguous amino acids of SEQ ID NO:3, wherein the at least eight contiguous amino acids have anti-viral activity, and an antiviral polypeptide comprising at least eight contiguous amino acids of SEQ ID NO:3, wherein the at least eight contiguous amino acids comprise amino acids 1-121 of SEQ ID NO:3, which have been rendered glycosylation-resistant and wherein the at least eight contiguous amino acids have antiviral activity, are also provided, as are conjugates comprising an aforementioned anti-viral polypeptide and at least one effector component. Compositions comprising an effective amount of an aforementioned anti-viral polypeptide or anti-viral polypeptide conjugate are also provided.

The invention further provides a method of inhibiting prophylactically or therapeutically a viral infection of a host, specifically a retroviral infection of a host, such as an infection of a host with a human immunodeficiency virus (HIV), e.g., HIV-1 or HIV-2, or influenza virus. The method comprises administering to the host an effective amount of an anti-viral polypeptide or anti-viral polypeptide conjugate comprising at least eight contiguous amino acids of SEQ ID NO:3, wherein the at least eight contiguous amino acids have anti-viral activity, whereupon the viral infection is inhibited.

Still further provided is a method of inhibiting a viral infection of an animal comprising transforming host cells in vivo with a nucleic acid molecule encoding an above-described polypeptide. Even still further provided is a method of inhibiting a viral infection of an animal comprising transforming host cells with a nucleic acid molecule encoding an above-described polypeptide and placing the transformed host cells into or onto the animal.

An antibody that binds griffithsin is provided as is a composition comprising same. Similarly, an anti-griffithsin antibody is provided as is a composition comprising same. A method of administering an anti-griffithsin antibody or a composition comprising same to a mammal so as to inhibit infection of the mammal with a virus is also provided.

BRIEF DESCRIPTION OF THE DRAWINGS

FIG. 1 is a flow diagram illustrating an anti-HIV bioassay-guided method of isolating, purifying, and elucidating the amino acid sequence of griffithsin.

FIG. 2 is a flow diagram illustrating a method of synthesizing a recombinant griffithsin gene.

FIG. 3 is a flow diagram illustrating a method of expressing a synthetic griffithsin gene encoding a His-tagged griffithsin polypeptide protein and purification of the recombinant His-tagged griffithsin.

FIG. 4*a* is a line graph illustrating the anti-HIV activity of native griffithsin, in terms of concentration of griffithsin (nM) (X-axis) versus % control (Y-axis). FIG. 4*b* is a line graph illustrating the anti-HIV activity of recombinant, His-tagged griffithsin in terms of concentration of griffithsin (nM) (X-axis) versus % control (Y-axis).

FIG. 5*a* is a bar graph comparing test proteins bound by griffithsin (Y-axis) and absorbance of the griffithsin-test protein complex at 405 nm (X-axis). FIG. 5*b* illustrates the concentration-dependent binding of griffithsin to glycosylated (•) or nonglycosylated (○) gp120 by comparing griffithsin (GRFT) concentration (pmol) and absorbance of griffithsin-gp120 complexes at 405 nm.

FIG. 6 is a flow diagram illustrating a method of producing anti-griffithsin antibodies.

FIG. 7 is the amino acid sequence of griffithsin polypeptide (SEQ ID NO:3) isolated and purified from Griffithsin sp.

FIG. 8 shows the nucleic acid (SEQ ID NO:1) sequence of recombinant griffithsin.

FIG. 9 is the amino acid sequence of a recombinant griffithsin polypeptide (SEQ ID NO:2).

FIG. 10 shows the nucleic acid sequence of a recombinant griffithsin polypeptide comprising a His tag (SEQ ID NO:4).

FIG. 11 is the amino acid sequence of a recombinant griffithsin polypeptide comprising a His tag (SEQ ID NO:5).

DETAILED DESCRIPTION OF THE PRESENT INVENTION

The principal overall objective of the invention is to provide an anti-viral polypeptide and derivatives thereof, and broad uses thereof (e.g., medical and research uses), including prophylactic and/or therapeutic applications against viruses. An initial observation, which led to the invention, was anti-viral activity of certain extracts from a marine organism, namely Rhodophyte (*Griffithsia* sp.), originally collected in the territorial waters of New Zealand. Low picomolar concentrations of a protein isolated from the extracts, referred to herein as griffithsin, irreversibly inactivated human clinical isolates of HIV. Its HIV molecular target is high mannose-comprised oligosaccharide constituents of Env glycoproteins. Upon binding, griffithsin inhibits viral binding, fusion, and entry. Griffithsin also targets other viruses having oligosaccharide constituents similar to HIV, such as other retroviruses, e.g., FIV, SIV and HTLV, and non-retroviruses, e.g., influenza, ebola, and measles.

Accordingly, the invention provides an isolated and purified anti-viral polypeptide of SEQ ID NO:3 from *Griffithsia* sp. and functional homologs thereof, referred to collectively as "griffithsin." Herein the term "griffithsin" is used generically to refer to a natural griffithsin or any related, functionally equivalent (i.e., anti-viral) polypeptide or derivative thereof. By definition, in this context, a related, functionally equivalent polypeptide or derivative thereof (a) contains a sequence of at least eight contiguous amino acids directly identical to a sub-sequence of eight contiguous amino acids contained within a natural griffithsin, and (b) can specifically bind to a virus, in particular an influenza virus or a retrovirus, more specifically a primate immunodeficiency virus, more specifically HIV-1, HIV-2 or SIV, or to an infected host cell expressing one or more viral antigen(s), more specifically an envelope glycoprotein, such as gp120, of the respective virus. In addition, such a functionally equivalent polypeptide or derivative thereof can comprise the amino acid sequence of a natural griffithsin (see SEQ ID NO:3), in which 1-20, preferably 1-10, more preferably 1, 2, 3, 4, or 5, and most preferably 1 or 2, amino acids have been removed from one or both ends, preferably from only one end, e.g., removed from the amino-terminal end, of natural griffithsin. Alternatively, a functionally equivalent polypeptide or derivative thereof can comprise the amino acid sequence of a native griffithsin (see SEQ ID NO:3), in which 1-20, preferably 1-10, more preferably 1, 2, 3, 4, or 5, and most preferably 1 or 2, amino acids have been added to one or both ends, preferably from only one end, e.g., the amino-terminal end, of the native griffithsin.

The invention further provides an isolated and purified polypeptide encoded by a nucleic acid molecule comprising a sequence of SEQ ID NO:1 or a nucleic acid molecule encoding an amino acid sequence of SEQ ID NO:2 or SEQ ID NO:3. Upon examination of the antiviral griffithsin polypeptide, the amino acid at position 31 of SEQ ID NO:3 (represented as Xaa) was found not to be a familiar amino acid residue. Placement of an alanine at position 31, such as achieved in the recombinant griffithsin polypeptide described herein (SEQ ID NO:2), results in a polypeptide exhibiting equivalent activity as the natural griffithsin polypeptide. If desired, the amino acid at position 31 can be substituted with any other amino acid to facilitate protein production. Ideally, the substitution at position 31 of SEQ ID NO:3 does not diminish the anti-viral activity of the protein (e.g., does not diminish the anti-viral activity more than 50%, more than 30% or more than 10%) as compared to the anti-viral activity of the native protein. Preferably, the aforementioned nucleic acid molecules encode at least eight (e.g., at least 10, at least 20, at least 30, at least 50, at least 70, at least 80, at least 90, or at least 100) contiguous amino acids of the amino acid sequence of SEQ ID NO:3, which desirably have anti-viral activity. If the at least eight contiguous amino acids of SEQ ID NO:3 comprise amino acids 1-121, desirably amino acid residue 45, 60, 71, and/or 104 has been rendered glycosylation resistant, while maintaining antiviral activity of the polypeptide.

The term "isolated" as used herein means having been removed from its natural environment. The term "purified" as used herein means having been increased in purity, wherein "purity" is a relative term and not to be construed as absolute purity. By "antiviral" is meant that the polypeptide or fragment thereof can inhibit a virus (e.g., inhibit entry of a virus into a host cell, limit the spread of viral infection by inhibiting cell to cell fusion, and the like), in particular an influenza virus, such as influenza virus or a strain A or strain B, or a retrovirus, specifically a primate immunodeficiency virus, more specifically a human immunodeficiency virus (HIV), such as HIV-1, HIV-2 or SIV.

Preferably, the polypeptide or derivative thereof comprises an amino acid sequence that is substantially homologous to that of an anti-viral protein from *Griffithsia* sp. By "substantially homologous" is meant sufficient homology to render the polypeptide or derivative thereof anti-viral, with anti-viral activity characteristic of an anti-viral protein isolated from *Griffithsia* sp. At least about 50% homology (e.g., at least about 60% homology, at least about 65% homology, or at least about 70% homology), preferably at least about 75% homology (e.g., at least about 80% homology or at least about 85% homology), and most preferably at least about 90% homology (e.g., at least about 95% homology) should exist.

Alterations of the natural amino acid sequence to produce variant polypeptides can be done by a variety of means known to those skilled in the art. For instance, amino acid substitutions can be conveniently introduced into the polypeptides at the time of synthesis. Alternatively, site-specific mutations can be introduced by ligating into an expression vector a synthesized oligonucleotide comprising the modified site. Alternately, oligonucleotide-directed, site-specific mutagenesis procedures can be used, such as disclosed in Walder et al., *Gene*, 42: 133 (1986); Bauer et al., *Gene*, 37: 73 (1985); Craik, *Biotechniques*, 12-19 (January 1995); and U.S. Pat. Nos. 4,518,584 and 4,737,462.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the ordinarily skilled artisan can readily group synthetic amino acids with naturally-occurring amino acids.

The ordinarily skilled artisan can generate griffithsin mutants or variants by, for example, substituting or mutating amino acids which are not critical for the anti-viral function of the polypeptide. Ideally, mutations that do not modify the electronic or structural environment of the peptide are generated to retain optimal antiviral activity. For example, natural griffithsin forms dimers, which can be advantageous in some embodiments. Therefore, alterations which do not disrupt dimer formation can be preferred. Amino acid residues which are not responsible for folding or stability of the three-dimensional conformation of the griffithsin polypeptide are candidate residues for mutation. Alternatively or in addition, amino acids which are not involved in glycoprotein binding can be mutated or replaced. It is understood that surface hydrophobicity plays a key role in protein-protein interactions and surface electrophilicity is important to protein-sugar interactions, such as the interaction between griffithsin and viral proteins. Hydrophobic surface clusters and electrophilic surface clusters on the griffithsin peptide or homologs which suggest regions critical for interaction with the viral envelope can be mapped using routine methods such as those disclosed in Bewley et al., *Nature Structural Biology*, 5(7): 571-578 (1998). Amino acid residues not found either in electrophilic or hydrophobic surface clusters are likely not critical for hydrophobicity or electrophilicity of these clusters and, thus, are appropriate targets for mutation to create griffithsin fragments (e.g., anti-viral polypeptides comprising at least about eight contiguous amino acids of SEQ ID NO:2 or SEQ ID NO:3), variants, mutants, or homologs (e.g., griffithsin variants having 80%, 85%, or 90% homology to SEQ ID NO:2 or SEQ ID NO:3) which retain antiviral activity. If desired, amino acid residues which are responsible for binding to high-mannose oligosaccharide-containing glycoproteins on the viral surface can be mutated to increase the specificity or affinity of glycoprotein binding.

If desired, the proteins and peptides of the invention (including antiviral fragments, variant polypeptides, fusion proteins, and conjugates) can be modified, for instance, by glycosylation, amidation, carboxylation, or phosphorylation, or by the creation of acid addition salts, amides, esters, in particular C-terminal esters, and N-acyl derivatives of the proteins of the invention. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the proteins, or at the N- or C-terminus. Desirably, such modifications and conjugations do not adversely affect the activity of the polypeptides (and variants thereof). While such modifications and conjugations can have greater or lesser activity, the activity desirably is not negated and is characteristic of the unaltered polypeptide.

The polypeptides (and fragments, homologs, variants, and fusion proteins) can be prepared by any of a number of conventional techniques. The polypeptide can be isolated or purified from a naturally occurring source or from a recombinant source. For instance, in the case of recombinant proteins, a DNA fragment encoding a desired polypeptide can be subcloned into an appropriate vector using well-known molecular genetic techniques (see, e.g., Maniatis et al., *Molecular Cloning: A Laboratory Manual*, 2nd ed. (Cold Spring Harbor Laboratory (1989)) and other references cited herein under "EXAMPLES"). The fragment can be transcribed and the polypeptide subsequently translated in vitro. Commercially available kits also can be employed (e.g., such as manufactured by Clontech, Palo Alto, Calif.; Amersham Life Sciences, Inc., Arlington Heights, Ill.; InVitrogen, San Diego, Calif.; and the like). The polymerase chain reaction optionally can be employed in the manipulation of nucleic acids.

Such polypeptides also can be synthesized using an automated peptide synthesizer in accordance with methods known in the art. Alternately, the polypeptide (and fragments, homologs, variants, and fusion proteins) can be synthesized using standard peptide synthesizing techniques well-known to those of skill in the art (e.g., as summarized in Bodanszky, *Principles of Peptide Synthesis*, (Springer-Verlag, Heidelberg:1984)). In particular, the polypeptide can be synthesized using the procedure of solid-phase synthesis (see, e.g., Merrifield, *J. Am. Chem. Soc.*, 85: 2149-54 (1963); Barany et al., *Int. J. Peptide Protein Res.*, 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be preformed in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation or through genetic means, such as are known to those skilled in the art. In this regard, the invention also provides a fusion protein comprising the isolated or purified antiviral polypeptide (or fragment thereof) or variant thereof and one or more other protein(s) having any desired properties or effector functions, such as cytotoxic or immunological properties, or other desired properties, such as to facilitate isolation, purification, analysis, or stability of the fusion protein.

A griffithsin conjugate comprising a griffithsin coupled to at least one effector component, which can be the same or different, is also provided. The effector component can be polyethylene glycol, dextran, albumin, an immunological reagent, a toxin, an antiviral agent, or a solid support matrix. "Immunological reagent" will be used to refer to an antibody, an antibody fragment (e.g., an F(ab')$_2$, an Fab', an Fab, an Fv, an sFv, a dsFv, or an Fc antibody fragment), an immunoglobulin, and an immunological recognition element. An immunological recognition element is an element, such as a peptide, e.g., the FLAG sequence of a recombinant griffithsin-FLAG fusion protein, which facilitates, through immunological recognition, isolation and/or purification and/or analysis of the protein or peptide to which it is attached. An immunological reagent also can be an immunogenic peptide, which can be fused to griffithsin for enhancing an immune response. In this respect, the invention provides an anti-viral conjugate comprising a griffithsin polypeptide or fragment thereof bound to a virus or viral envelope glycoprotein. A griffithsin fusion protein is a type of griffithsin conjugate, wherein a griffithsin is coupled to one or more other protein(s) having any desired properties or effector functions, such as cytotoxic or immunological properties, or other desired properties, such as to facilitate isolation, purification or analysis of the fusion protein or increase the stability or in vivo half-life of the fusion protein. Griffithsin also can be attached to a chemical moiety which allows recognition, isolation, purification, and/or analysis of the protein or peptide. An example of such a chemical moiety is a His tag of a recombinant griffithsin-His fusion protein.

A "toxin" can be, for example, *Pseudomonas* exotoxin. An "antiviral agent" can be AZT, ddI, ddC, 3TC gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, gramicidin, amantatadine, rimantadine, and neuraminidase inhibitors, and cyanovirin-N or a functional homolog or derivative thereof (see, for example, U.S. Pat. No. 5,843,882). A "solid support matrix" can be a magnetic bead, a flow-through matrix, a sponge, a stent, a culture plate, or a matrix comprising a contraceptive device, such as a condom, diaphragm, cervical cap, vaginal ring or contraceptive sponge. In an alternative embodiment, a solid support matrix can be an implant for surgical implantation in a host and, if appropriate, later removal.

In view of the foregoing, the invention further provides a composition comprising (i) the isolated or purified antiviral polypeptide (or fragment thereof), a variant thereof, a fusion protein of the antiviral polypeptide (or fragment thereof) or variant thereof, and a conjugate of the antiviral polypeptide (or fragment thereof) or variant thereof, and/or (ii) a carrier, excipient or adjuvant therefor. Preferably, component (i) of the composition is present in an antiviral effective amount and the carrier is pharmaceutically acceptable. By "antiviral effective amount" is meant an amount sufficient to inhibit the infectivity of the virus.

The carrier can be any of those conventionally used and is limited only by chemico-physical considerations, such as solubility and lack of reactivity with the active agent of the invention, and by the route of administration. It is preferred that the pharmaceutically acceptable carrier be one which is chemically inert to the active agent and one which has no detrimental side effects or toxicity under the conditions of use. The pharmaceutically acceptable carriers described herein, for example, vehicles, adjuvants, excipients, and diluents, are well-known to those ordinarily skilled in the art and are readily available to the public. Typically, the composition, such as a pharmaceutical composition, can comprise a physiological saline solution; dextrose or other saccharide solution; or ethylene, propylene, polyethylene, or other glycol. The pharmaceutical composition preferably does not comprise mannose or N-acetyl-glucosamine, as these molecules may interfere with the functioning of the antiviral agent.

The invention also provides a method of obtaining a griffithsin from *Griffithsia* sp. Such a method comprises (a) identifying an extract of *Griffithsia* sp. containing anti-viral activity, (b) optionally removing high molecular weight biopolymers from the extract, (c) anti-viral bioassay-guided fractionating the extract to obtain a crude extract of griffithsin, and (d) purifying the crude extract by reverse-phase HPLC to obtain griffithsin (see, also, Example 1). More specifically, the method involves the use of ethanol to remove high molecular weight biopolymers from the extract and the use of an anti-HIV bioassay to guide fractionation of the extract.

Griffithsin (a polypeptide of exactly SEQ ID NO:3), which was isolated and purified using the aforementioned method, was subjected to conventional procedures typically used to determine the amino acid sequence of a given pure protein. Thus, the griffithsin was initially sequenced by N-terminal Edman degradation of intact protein and numerous overlapping peptide fragments generated by endoproteinase digestion. Amino acid analysis was in agreement with the deduced sequence. ESI mass spectrometry of reduced, HPLC-purified griffithsin showed a molecular ion consistent with the calculated value. These studies indicated that griffithsin from *Griffithsia* was comprised of a unique sequence of 121 amino acids having little or no significant homology or identity to previously described proteins or transcription products of known nucleotide sequences. No more than eight contiguous amino acids from griffithsin were found in any amino acid sequences from known proteins, nor were there any known proteins from any source having significant sequence identity with griffithsin. Given the chemically deduced amino acid sequence of griffithsin, a corresponding recombinant griffithsin (r-griffithsin) was created and used to establish definitively that the deduced amino acid sequence was, indeed, active against virus, such as HIV and influenza.

Accordingly, the invention provides isolated and purified nucleic acid molecules and synthetic nucleic acid molecules, which comprise a coding sequence for a griffithsin, such as an isolated and purified nucleic acid molecule comprising a sequence of SEQ ID NO:1, an isolated and purified nucleic acid molecule encoding an amino acid sequence of SEQ ID NO:2, an isolated and purified nucleic acid sequence encoding an amino acid sequence SEQ ID NO:3, an isolated and purified nucleic acid molecule comprising a sequence of SEQ ID NO:4, an isolated and purified nucleic acid sequence encoding an amino acid sequence of SEQ ID NO:5, and a nucleic acid molecule that is substantially homologous or substantially identical to any one of the aforementioned nucleic acid molecules. By "substantially homologous" is meant sufficient homology to render the polypeptide or derivative thereof anti-viral, with anti-viral activity characteristic of an anti-viral protein isolated from *Griffithsia*. At least about 50% homology or identity (e.g., at least about 60%, at least about 65%, or at least about 70% homology or identity), preferably at least about 75% homology or identity (e.g., at least about 80% or at least about 85% homology or identity), and most preferably at least about 90% homology or identity (e.g., at least about 95% homology or identity) should exist.

The inventive nucleic acid molecule preferably comprises a nucleic acid sequence encoding at least eight (preferably at least 10, more preferably at least 20, and most preferably at least 30) contiguous amino acids of the amino acid sequence of SEQ ID NO:3 or SEQ ID NO:2. The inventive nucleic acid molecule also comprises a nucleic acid sequence encoding a polypeptide comprising the amino acid sequence of a native griffithsin, in which 1-20, preferably 1-10, more preferably 1, 2, 3, 4, or 5, and most preferably 1 or 2, amino acids have been removed from one or both ends, preferably from only one end, e.g., removed from the amino-terminal end, of the native griffithsin. Alternatively, the nucleic acid molecule can comprise a nucleic acid sequence encoding a polypeptide comprising the amino acid sequence of a natural griffithsin (see SEQ ID NO:3), in which 1-20, preferably 1-10, more preferably 1, 2, 3, 4, or 5, and most preferably 1 or 2, amino acids have been added to one or both ends, preferably from only one end, e.g., the amino-terminal end, of the native griffithsin. Preferably, the isolated and purified nucleic acid molecule encodes a polypeptide comprising at least eight contiguous amino acids of SEQ ID NO:3, which desirably have anti-viral activity. If the at least eight contiguous amino acids comprise amino acids 1-121 of SEQ ID NO:3, desirably amino acids 46, 60, 71, and/or 104 have been rendered glycosylation resistant, while maintaining antiviral activity of the polypeptide. Deletions and substitutions of SEQ ID NO:2 or SEQ ID NO:3 are within the skill in the art.

Given the present disclosure, it will be apparent to one skilled in the art that a partial griffithsin gene sequence will likely suffice to code for a fully functional, i.e., anti-viral, such as anti-influenza or anti-HIV, griffithsin. A minimum essential DNA coding sequence(s) for a functional griffithsin can readily be determined by one skilled in the art, for example, by synthesis and evaluation of sub-sequences comprising the native griffithsin, and by site-directed mutagenesis studies of the griffithsin DNA coding sequence.

Using an appropriate DNA coding sequence, a recombinant griffithsin can be made by genetic engineering techniques (for general background see, e.g., Nicholl, in *An Introduction to Genetic Engineering*, Cambridge University Press: Cambridge (1994), pp. 1-5 & 127-130; Steinberg et al., in *Recombinant DNA Technology Concepts and Biomedical Applications*, Prentice Hall: Englewood Cliffs, N.J. (1993), pp. 81-124 & 150-162; Sofer in *Introduction to Genetic Engineering*, Butterworth-Heinemann, Stoneham, Mass. (1991), pp. 1-21 & 103-126; Old et al., in *Principles of Gene Manipulation*, Blackwell Scientific Publishers: London (1992), pp. 1-13 & 108-221; and Emtage, in *Delivery Systems for Peptide Drugs*, Davis et al., eds., Plenum Press: New York (1986), pp. 23-33). For example, a *Griffithsia* gene or cDNA encoding a griffithsin can be identified and subcloned. The gene or cDNA then can be incorporated into an appropriate expression vector and delivered into an appropriate polypeptide-synthesizing organism (e.g., *E. coli*, *S. cerevisiae*, *P. pastoris*, or other bacterial, yeast, insect, plant or mammalian cells), where the gene, under the control of an endogenous or exogenous promoter, can be appropriately transcribed and translated. Alternatively, the expression vector can be administered to a plant or animal, for example, for large-scale production (see, e.g., Fischer et al., *Transgenic Res.*, 9 (4-5):279-299 (2000); Fischer et al., *J. Biol. Regul. Homeost. Agents*, 14: 83-92 (2000); deWilde et al., *Plant Molec. Biol.*, 43: 347-359 (2000); Houdebine, *Transgenic Research*, 9: 305-320 (2000); Brink et al., *Theriogenology*, 53: 139-148 (2000); Pollock et al., *J. Immunol. Methods*, 231: 147-157 (1999); Conrad et al., *Plant Molec. Biol.*, 38: 101-109 (1998); Staub et al., *Nature Biotech.*, 18: 333-338 (2000); McCormick et al., *PNAS USA*, 96: 703-708 (1999); Zeitlin et al., *Nature Biotech.*, 16: 1361-1364 (1998); Tacker et al., *Microbes and Infection*, 1: 777-783 (1999); Tacket et al., *Nature Med.*, 4(5):607-609 (1998); and *Methods in Biotechnology, Recombinant Proteins from Plants, Production and Isolation of Clinically Useful Compounds*, Cunningham and Porter, eds., Humana Press: Totowa, N.J. (1998)). Such expression vectors (including, but not limited to, phage, cosmid, viral, and plasmid vectors) are known to those skilled in the art, as are reagents and techniques appropriate for gene transfer (e.g., transfection, electroporation, transduction, micro-injection, transformation, etc.). If a griffithsin is to be recombinantly produced in isolated eukaryotic cells or in a eukaryotic organism, such as a plant (see above references and also *Methods in Biotechnology, Recombinant Proteins from Plants, Production and Isolation of Clinically Useful Compounds*, Cunningham and Porter, eds., Humana Press: Totowa, N.J. (1998)), desirably the N-linked glycosylation sites at positions 45, 60, 71, and/or 104 is rendered glycosylation-resistant, such as in accordance with the methods described herein. Subsequently, the recombinantly produced polypeptide can be isolated and purified using standard techniques known in the art (e.g., chromatography, centrifugation, differential solubility, isoelectric focusing, etc.), and assayed for anti-viral activity.

Alternatively, a natural griffithsin can be obtained from *Griffithsia* by non-recombinant methods, and sequenced by conventional techniques. The sequence can then be used to synthesize the corresponding DNA, which can be subcloned into an appropriate expression vector and delivered into a polypeptide-producing cell for en mass recombinant production of the desired polypeptide.

In this regard, the invention also provides a vector comprising a DNA sequence, e.g., a *Griffithsia* gene sequence for griffithsin, a cDNA encoding a griffithsin, or a synthetic DNA sequence encoding griffithsin. The vector can be targeted to a cell-surface receptor if so desired. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology, Vol.* 153, Wu and Grossman, eds., Academic Press (1987) and the references cited herein under "EXAMPLES"). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid as described above or a portion thereof ligated to a replication system functional in a prokaryotic or eukaryotic host cell. Replication systems can be derived from ColE1, 2 mµ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

One of ordinary skill in the art will appreciate that any of a number of vectors known in the art are suitable for use in the invention. Suitable vectors include those designed for propagation and expansion or for expression or both. Examples of suitable vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, and adenovirus-based vectors. Any of these expression constructs can be prepared using standard recombinant DNA techniques described in, e.g., Sambrook et al., *Molecular Cloning: A Laboratory Manual*, 2$^{nd}$ edition, Cold Spring Harbor Laboratory Press, Cold Spring Harbor, N.Y. (1989); Ausubel et al., *Current Protocols in Molecular Biology*, Greene Publishing Associates and John Wiley & Sons, New York, N.Y. (1994); Fischer et al., *Transgenic Res.*, 9 (4-5): 279-299 (2000); Fischer et al., *J. Biol. Regul. Homeost. Agents*, 14: 83-92 (2000); deWilde et al., *Plant Molec. Biol.*, 43: 347-359 (2000); Houdebine, *Transgenic Research*, 9: 305-320 (2000); Brink et al., *Theriogenology*, 53: 139-148 (2000); Pollock et al., *J. Immunol. Methods*, 231: 147-157 (1999); Conrad et al., *Plant Molec. Biol.*, 38: 101-109 (1998); Staub et al., *Nature Biotech.*, 18: 333-338 (2000); McCormick et al., *PNAS USA*, 96: 703-708 (1999); Zeitlin et al., *Nature Biotech.*, 16: 1361-1364 (1998); Tacker et al., *Microbes and Infection*, 1: 777-783 (1999); and Tacket et al.,

*Nature Med.,* 4(5):607-609 (1998). Examples of cloning vectors include the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAMneo (Clonetech).

An expression vector can comprise a native or normative promoter operably linked to an isolated or purified nucleic acid as described above. The selection of promoters, e.g., strong, weak, inducible, tissue-specific and developmental-specific, is within the skill in the art. Similarly, the combining of a nucleic acid molecule as described above with a promoter is also within the skill in the art.

The DNA, whether isolated and purified or synthetic, or cDNA encoding a griffithsin can encode for either the entire griffithsin or a portion thereof. Where the DNA or cDNA does not comprise the entire coding sequence of the native griffithsin, the DNA or cDNA can be subcloned as part of a gene fusion. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

Genes also can be constructed for specific fusion proteins containing a functional griffithsin component plus a fusion component conferring additional desired attribute(s) to the composite protein. For example, a fusion sequence for a toxin or immunological reagent can be added to facilitate purification and analysis of the functional protein.

Genes can be specifically constructed to code for fusion proteins, which contain a griffithsin coupled to an effector protein, such as a toxin or immunological reagent, for specific targeting to a virus or viral-infected cells, e.g., HIV and/or HIV-infected cells or influenza and/or influenza-infected cells. In these instances, the griffithsin moiety serves not only as a neutralizing agent but also as a targeting agent to direct the effector activities of these molecules selectively against a given virus, such as HIV or influenza. Thus, for example, a therapeutic agent can be obtained by combining the HIV-targeting function or influenza-targeting function of a functional griffithsin with a toxin aimed at neutralizing infectious virus and/or by destroying cells producing infectious virus, such as HIV or influenza. Similarly, a therapeutic agent can be obtained, which combines the viral-targeting function of a griffithsin with the multivalency and effector functions of various immunoglobulin subclasses. Example 6 further illustrates the viral-targeting, specifically gp120-targeting, properties of a griffithsin.

Similar rationales underlie extensive developmental therapeutic efforts exploiting the HIV gp120-targeting properties of sCD4. For example, sCD4-toxin conjugates have been prepared in which sCD4 is coupled to a *Pseudomonas* exotoxin component (Chaudhary et al., in *The Human Retrovirus*, Gallo et al., eds., Academic Press: San Diego, Calif. (1991), pp. 379-387; and Chaudhary et al., *Nature,* 335: 369-372 (1988)), or to a diphtheria toxin component (Aullo et al., *EMBO J.,* 11: 575-583 (1992)) or to a ricin A-chain component (Till et al., *Science,* 242: 1166-1167 (1988)). Likewise, sCD4-immunoglobulin conjugates have been prepared in attempts to decrease the rate of in vivo clearance of functional sCD4 activity, to enhance placental transfer, and to effect a targeted recruitment of immunological mechanisms of pathogen elimination, such as phagocytic engulfment and killing by antibody-dependent cell-mediated cytotoxicity, to kill and/or remove HIV-infected cells and virus (Capon et al., *Nature,* 337: 525-531 (1989); Traunecker et al., *Nature,* 339: 68-70 (1989); and Langner et al. (1993), supra). While such CD4-immunoglobulin conjugates (sometimes called "immunoadhesins") have, indeed, shown advantageous pharmacokinetic and distributional attributes in vivo, and anti-HIV effects in vitro, clinical results have been discouraging (Schooley et al. (1990), supra; Husson et al. (1992), supra; and Langner et al. (1993), supra). This is not surprising since clinical isolates of HIV, as opposed to laboratory strains, are highly resistant to binding and neutralization by sCD4 (Orloff et al. (1995), supra; and Moore et al. (1992), supra). The griffithsin polypeptide binds to a wide range of sugars present on viral glycoproteins and, therefore, can inhibit a wide range of viruses which display those glycoproteins. The extraordinarily broad targeting properties of a functional griffithsin to viruses, e.g., primate retroviruses, in general, and clinical and laboratory strains, in particular, can be especially advantageous for combining with toxins, immunoglobulins and other selected effector proteins.

Viral-targeted conjugates can be prepared either by genetic engineering techniques (see, for example, Chaudhary et al. (1988), supra) or by chemical coupling of the targeting component with an effector component. The most feasible or appropriate technique to be used to construct a given griffithsin conjugate or fusion protein will be selected based upon consideration of the characteristics of the particular effector molecule selected for coupling to a griffithsin. For example, with a selected non-proteinaceous effector molecule, chemical coupling, rather than genetic engineering techniques, may be the only feasible option for creating the desired griffithsin conjugate.

Accordingly, the invention also provides nucleic acid molecules encoding griffithsin fusion proteins. In particular, the invention provides a nucleic acid molecule comprising SEQ ID NO:4 and substantially homologous sequences thereof. Also provided is a vector comprising a nucleic acid sequence encoding a griffithsin fusion protein and a method of obtaining a griffithsin fusion protein by expression of the vector encoding a griffithsin fusion protein in a protein-synthesizing organism as described above. Accordingly, griffithsin fusion proteins are also provided.

In view of the above, the invention further provides an isolated and purified nucleic acid molecule, which comprises a griffithsin coding sequence, such as one of the aforementioned nucleic acids, namely a nucleic acid molecule encoding an amino acid sequence of SEQ ID NO:2 or SEQ ID NO:3 or a nucleic acid molecule comprising a sequence of SEQ ID NO:1 coupled to a second nucleic acid encoding an effector protein. The first nucleic acid preferably comprises a nucleic acid sequence encoding at least eight contiguous amino acids of the amino acid sequence of SEQ ID NO:2 or SEQ ID NO:3, which encodes a functional griffithsin, and the second nucleic acid preferably encodes an effector protein, such as a toxin or immunological reagent as described herein.

Accordingly, the invention also further provides an isolated and purified fusion protein encoded by a nucleic acid molecule comprising a sequence of SEQ ID NO:1 or a nucleic acid molecule encoding an amino acid sequence of SEQ ID NO:2 or SEQ ID NO: 3, either one of which is coupled to a second nucleic acid encoding an effector protein. Preferably, the aforementioned nucleic acid molecules encode at least eight contiguous amino acids of the amino acid sequence of SEQ ID NO:2 or SEQ ID NO:3, which desirably have antiviral activity, coupled to an effector molecule, such as a toxin or immunological reagent as described above. Preferably, the effector molecule targets a virus, more preferably HIV or influenza, and, most preferably glycoprotein gp120 of HIV or hemagluttinin of influenza. If the at least eight contiguous amino acids of SEQ ID NO:3 (or SEQ ID NO:2) comprise amino acids 1-121, desirably amino acids 46, 60, 71, and/or 104 have been rendered glycosylation-resistant, yet maintain antiviral activity by substitution of the asparagine at those positions with, for example, an alanine or a glutamine residue.

The coupling can be effected at the DNA level or by chemical coupling as described above. For example, a griffithsin-effector protein conjugate of the invention can be obtained by (a) selecting a desired effector protein or peptide; (b) synthesizing a composite DNA coding sequence comprising a first DNA coding sequence comprising one of the aforementioned nucleic acid sequences, which codes for a functional griffithsin, coupled to a second DNA coding sequence for an effector protein or peptide, e.g., a toxin or immunological reagent; (c) expressing said composite DNA coding sequence in an appropriate protein-synthesizing organism; and (d) purifying the desired fusion protein to substantially pure form. Alternatively, a griffithsin-effector molecule conjugate of the invention can be obtained by (a) selecting a desired effector molecule and a griffithsin or griffithsin fusion protein; (b) chemically coupling the griffithsin or griffithsin fusion protein to the effector molecule; and (c) purifying the desired griffithsin-effector molecule conjugate to substantially pure form.

Conjugates comprising a functional griffithsin (e.g., an anti-viral polypeptide comprising at least eight contiguous amino acids of SEQ ID NO:3, such as SEQ ID NO:3, wherein the at least eight contiguous amino acids bind to a virus, in particular an infectious virus, such as influenza virus or HIV, in which case the griffithsin binds to gp120 or hemagluttinin) coupled to an anti-griffithsin antibody, a virus, a viral glycoprotein, or at least one effector component, which can be the same or different, such as a toxin, an immunological reagent, an antiviral agent, or other functional reagent, can be designed even more specifically to exploit the unique viral targeting, e.g., gp120-targeting properties, of griffithsins.

Other functional reagents that can be used as effector components in the inventive conjugates can include, for example, polyethylene glycol, dextran, albumin, a solid support matrix, and the like, whose intended effector functions may include one or more of the following: to improve stability of the conjugate; to increase the half-life of the conjugate; to increase resistance of the conjugate to proteolysis; to decrease the immunogenicity of the conjugate; to provide a means to attach or immobilize a functional griffithsin onto a solid support matrix (e.g., see, for example, Harris, in *Poly (Ethylene Glycol) Chemistry: Biotechnical and Biomedical Applications*, Harris, ed., Plenum Press: New York (1992), pp. 1-14). Conjugates furthermore can comprise a functional griffithsin coupled to more than one effector molecule, each of which, optionally, can have different effector functions (e.g., such as a toxin molecule (or an immunological reagent) and a polyethylene glycol (or dextran or albumin) molecule). Diverse applications and uses of functional proteins and peptides, such as in the present instance a functional griffithsin, attached to or immobilized on a solid support matrix, are exemplified more specifically for poly(ethylene glycol) conjugated proteins or peptides in a review by Holmberg et al. (In *Poly(Ethylene Glycol) Chemistry: Biotechnical and Biomedical Applications*, Harris, ed., Plenum Press: New York (1992), pp. 303-324). Preferred examples of solid support matrices include magnetic beads, a flow-through matrix, and a matrix comprising a contraceptive device, such as a condom, a diaphragm, a cervical cap, a vaginal ring or a sponge.

Example 4 reveals novel gp120-directed effects of griffithsins. Solid-phase ELISA experiments show that griffithsin is capable of global conformational effects on gp120, as observed as a decrease of immunoreactivity at multiple, distinct, non-overlapping epitopes.

The range of anti-viral activity of griffithsin against diverse $CD4^+$-tropic immunodeficiency virus strains in various target cells is remarkable; virtually all tested strains of HIV-1, HIV-2 and SIV were similarly sensitive to griffithsin; clinical isolates and laboratory strains showed essentially equivalent sensitivity. Cocultivation of chronically infected and uninfected CEM-SS cells with griffithsin did not inhibit viral replication, but did cause a concentration-dependent inhibition of cell-to-cell fusion and virus transmission; similar results from binding and fusion inhibition assays employing HeLa-CD4-LTR-β-galactosidase cells were consistent with griffithsin inhibition of virus-cell and/or cell-cell binding.

The anti-viral, e.g., anti-HIV, activity of the griffithsins and conjugates thereof of the invention can be further demonstrated in a series of interrelated in vitro anti-viral assays (Gulakowski et al., *J. Virol. Methods*, 33: 87-100 (1991)), which accurately predict for anti-viral activity in humans. These assays measure the ability of compounds to prevent the replication of HIV and/or the cytopathic effects of HIV on human target cells. These measurements directly correlate with the pathogenesis of HIV-induced disease in vivo. The results of the analysis of the anti-viral activity of griffithsins or conjugates, as set forth in Examples 5-7 and 9, predict accurately the anti-viral activity of these products in vivo in humans and, therefore, establish the utility of the invention. Furthermore, since the invention also provides methods of ex vivo use of griffithsins and conjugates, the utility of griffithsins and conjugates thereof is even more certain.

The griffithsins and conjugates thereof of the invention can be shown to inhibit a virus, specifically a retrovirus, more specifically an immunodeficiency virus, such as the human immunodeficiency virus, i.e., HIV-1 or HIV-2. The griffithsins and conjugates of the invention can be used to inhibit other retroviruses as well as other viruses (see, e.g., *Principles of Virology: Molecular Biology, Pathogenesis, and Control*, Flint et al., eds., ASM Press: Washington, D.C. (2000), particularly Chapter 19). Examples of viruses that may be treated in accordance with the invention include, but are not limited to, Type C and Type D retroviruses, HTLV-1, HTLV-2, HIV, FIV, FLV, SIV, MLV, BLV, BIV, equine infectious virus, anemia virus, avian sarcoma viruses, such as Rous sarcoma virus (RSV), hepatitis type A, B, non-A and non-B viruses, arboviruses, varicella viruses, human herpes virus (e.g., HHV-6), measles, mumps, filovirus (e.g., Ebola, such as Ebola strains Sudan, Zaire, Cote d'Ivoire, and Reston) and rubella viruses. Griffithsins and conjugate thereof also can be used to inhibit influenza viral infection (see, e.g., *Fields Virology*, third edition, Fields et al., eds., Lippincott-Raven Publishers: Philadelphia, Pa. (1996), particularly Chapter 45) prophylactically and therapeutically in accordance with the methods set forth herein.

Thus, the invention further provides a composition comprising (i) one or more of an above-described purified or isolated nucleic acid or variant thereof, optionally as part of an encoded fusion protein, and (ii) a carrier, excipient or adjuvant. Preferably, (i) is present in an antiviral effective amount and the composition is pharmaceutically acceptable. The composition can further comprise at least one additional active agent, such as an antiviral agent other than a griffithsin (or antiviral fragment, fusion protein or conjugate thereof), in an antiviral effective amount. Suitable antiviral agents include AZT, ddA, ddI, ddC, 3TC gancyclovir, fluorinated dideoxynucleosides, acyclovir, α-interferon, nonnucleoside analog compounds, such as nevirapine (Shih et al., PNAS, 88: 9878-9882, (1991)), TIBO derivatives, such as R82913 (White et al., Antiviral Res., 16: 257-266 (1991)), Ro31-8959, BI-RJ-70 (Merigan, Am. J. Med., 90 (Suppl. 4A):8S-17S (1991)), michellamines (Boyd et al., J. Med. Chem., 37: 1740-1745 (1994)) and calanolides (Kashman et al., J. Med. Chem., 35: 2735-2743 (1992)), nonoxynol-9, gossypol and derivatives, gramicidin, Enfurtide (i.e., T20), cyanovirin-N and functional homologs thereof (Boyd et al. (1997), supra). Other exemplary antiviral compounds include protease inhibitors (see R. C. Ogden and C. W. Flexner, eds., Protease Inhibitors in AIDS Therapy, Marcel Dekker, N Y (2001)), such as saquinavir (see I. B. Duncan and S. Redshaw, in R. C. Ogden and C. W. Flexner, supra, pp. 27-48), ritonavir (see D. J. Kempf, in R. C. Ogden and C. W. Flexner, supra, pp. 49-64), indinavir (see B. D. Dorsey and J. P. Vacca, in R. C. Ogden and C. W. Flexner, supra, pp. 65-84), nelfinavir (see S. H. Reich, in R. C. Ogden and C. W. Flexner, supra, pp. 85-100), amprenavir (see R. D. Tung, in R. C. Ogden and C. W. Flexner, supra, pp. 101-118), and anti-TAT agents. If the composition is to be used to induce an immune response, it comprises an immune response-inducing amount of the inventive agent and can further comprise an immunoadjuvant, such as polyphosphazene polyelectrolyte.

The pharmaceutical composition can contain other pharmaceuticals, such as virucides, immunomodulators, immunostimulants, antibiotics and absorption enhancers. Exemplary immunomodulators and immunostimulants include various interleukins, sCD4, cytokines, antibody preparations, blood transfusions, and cell transfusions. Exemplary antibiotics include antifungal agents, antibacterial agents, and anti-Pneumocystitis carnii agents. Exemplary absorption enhancers include bile salts and other surfactants, saponins, cyclodextrins, and phospholipids (Davis (1992), supra).

An isolated cell comprising an above-described purified or isolated nucleic acid or variant thereof, optionally in the form of a vector, which is optionally targeted to a cell-surface receptor, is also provided. Examples of host cells include, but are not limited to, a human cell, a human cell line, E. coli, B. subtilis, P. aerugenosa, S. cerevisiae, and N. crassa. E. coli, in particular E. coli TB-1, TG-2, DH5α, XL-Blue MRF' (Stratagene), SA2821 and Y1090. Preferably, the cell is a mammalian cell, bacterium, or yeast. A preferred bacterium is lactobacillus or other commensal microorganism. The above-described nucleic acid or variant thereof, optionally in the form of a vector, can be introduced into a host cell using such techniques as transfection, electroporation, transduction, micro-injection, transformation, and the like.

Accordingly, the invention provides a method of inhibiting prophylactically or therapeutically a viral infection, in particular an influenza viral infection or HIV infection, of a host. The method comprises administering to the host an effective amount of an anti-viral polypeptide or anti-viral polypeptide conjugate comprising at least eight contiguous amino acids of SEQ ID NO:3, wherein the at least eight contiguous amino acids are nonglycosylated and have anti-viral activity, whereupon the viral infection is inhibited. The anti-viral polypeptide can be derived from a griffithsin obtained from Griffithsia or recombinantly produced in accordance with the methods described above. Nonglycosylated anti-viral polypeptides can be produced in prokaryotic cells/organisms. Amino acids 45, 60, 71, and/or 104 in such nonglycosylated antiviral polypeptides can be deleted or substituted, for example, with alanine or glutamine. Nonglycosylated antiviral polypeptides also can be produced in eukaryotic cells/organisms by expressing a portion of a griffithsin, such as that of SEQ ID NO:3, that does not contain a glycosylation site or all or a portion of a griffithsin, such as that of SEQ ID NO:3, which contains a glycosylation site that has been rendered glycosylation-resistant as described and exemplified herein. When the viral infection is an influenza viral infection and the anti-viral polypeptide or anti-viral polypeptide conjugate is administered topically to the host, preferably the anti-viral protein or anti-viral peptide is administered to the respiratory system of the host, preferably as an aerosol or microparticulate powder.

The prophylactic and therapeutic treatment of many viral infections, including influenza virus infections, is complicated by appearance of virus forms resistant to currently employed medications, such as neurominidase inhibitors. The inventive method is particularly useful in this context, as the inventive anti-viral polypeptide or anti-viral polypeptide conjugate binds a wide range of glycoproteins present on the viral surface. Accordingly, the inventive anti-viral polypeptide or conjugate thereof can be administered to an animal, preferably a human, dog, cat, bird, cow, pig, horse, lamb, mouse, or rat, in combination with other anti-viral agents to guard against the propagation of anti-viral-resistant strains of virus. In addition, it is thought that during adaptive mutation (e.g., resistance to neuraminidase inhibitors), the level of glycosylation found at the viral surface increases in some viruses, such as influenza. Thus, in that the inventive anti-viral agent binds sugars of viral surface glycoproteins, the inventive method provides a valuable complimentary therapy to current anti-viral regimens.

Griffithsins and conjugates thereof collectively comprise polypeptides and proteins, and, as such, are particularly susceptible to hydrolysis of amide bonds (e.g., catalyzed by peptidases) and disruption of essential disulfide bonds or formation of inactivating or unwanted disulfide linkages (Carone et al., J. Lab. Clin. Med., 100:1-14 (1982)). There are various ways to alter molecular structure, if necessary, to provide enhanced stability to the griffithsin or conjugate thereof (Wunsch, Biopolymers, 22: 493-505 (1983); and Samanen, in Polymeric Materials in Medication, Gebelein et al., eds., Plenum Press: New York (1985) pp. 227-242), which may be essential for preparation and use of pharmaceutical compositions containing griffithsins or conjugates thereof for therapeutic or prophylactic applications against viruses, e.g., HIV. Possible options for useful chemical modifications of a griffithsin or conjugate include, but are not limited to, the following (adapted from Samanen, J. M. (1985) supra): (a) olefin substitution, (b) carbonyl reduction, (c) D-amino acid substitution, (d) N-methyl substitution, (e) C-methyl substitution, (f) C—C'-methylene insertion, (g) dehydro amino acid insertion, (h) retro-inverso modification, (i) N-terminal to C-terminal cyclization, and (j) thiomethylene modification. Griffithsins and conjugates thereof also can be modified by covalent attachment of carbohydrate and polyoxyethylene derivatives, which are expected to enhance stability and resistance to proteolysis (Abuchowski et al., in Enzymes as Drugs, Holcenberg et al., eds., John Wiley: New York (1981), pp. 367-378).

Other important general considerations for design of delivery strategy systems and compositions, and for routes of administration, for protein and peptide drugs, such as griffithsins and conjugates thereof (Eppstein, *CRC Crit. Rev. Therapeutic Drug Carrier Systems*, 5: 99-139 (1988); Siddiqui et al., *CRC Crit. Rev. Therapeutic Drug Carrier Systems*, 3: 195-208 (1987); Banga et al., *Int. J. Pharmaceutics*, 48: 15-50 (1988); Sanders, *Eur. J. Drug Metab. Pharmacokinetics*, 15: 95-102 (1990); and Verhoef, *Eur. J. Drug Metab. Pharmacokinetics*, 15: 83-93 (1990)), also apply. The appropriate delivery system for a given griffithsin or conjugate thereof will depend upon its particular nature, the particular clinical application, and the site of drug action. As with any protein or peptide drug, oral delivery of a griffithsin or a conjugate thereof will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it will be necessary to use an absorption-enhancing agent in combination with a given griffithsin or conjugate thereof A wide variety of absorption-enhancing agents have been investigated and/or applied in combination with protein and peptide drugs for oral delivery and for delivery by other routes (Verhoef (1990), supra; van Hoogdalem, *Pharmac. Ther.*, 44: 407-443 (1989); and Davis, *J. Pharm. Pharmacol*, 44 (Suppl. 1):186-190 (1992)). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides and diglycerides, (e) non-surfactants, such as unsaturated cyclic ureas, (f) saponins, (g) cyclodextrins, and (h) phospholipids.

Other approaches to enhancing oral delivery of protein and peptide drugs, such as the griffithsins and conjugates thereof, can include aforementioned chemical modifications to enhance stability to gastrointestinal enzymes and/or increased lipophilicity. Alternatively, or in addition, the protein or peptide drug can be administered in combination with other drugs or substances, which directly inhibit proteases and/or other potential sources of enzymatic degradation of proteins and peptides. Yet another alternative approach to prevent or delay gastrointestinal absorption of protein or peptide drugs, such as griffithsins or conjugates, is to incorporate them into a delivery system that is designed to protect the protein or peptide from contact with the proteolytic enzymes in the intestinal lumen and to release the intact protein or peptide only upon reaching an area favorable for its absorption. A more specific example of this strategy is the use of biodegradable microcapsules or microspheres, both to protect vulnerable drugs from degradation, as well as to effect a prolonged release of active drug (Deasy, in *Microencapsulation and Related Processes*, Swarbrick, ed., Marcell Dekker, Inc.: New York (1984), pp. 1-60, 88-89, 208-211). Microcapsules also can provide a useful way to effect a prolonged delivery of a protein and peptide drug, such as a griffithsin or conjugate thereof, after injection (Maulding, *J. Controlled Release*, 6: 167-176 (1987)).

Given the aforementioned potential complexities of successful oral delivery of a protein or peptide drug, it is fortunate that there are numerous other potential routes of delivery of a protein or peptide drug, such as a griffithsin or conjugate thereof. These routes include topical, subcutaneous, intravenous, intraarterial, intrathecal, intracisternal, buccal, rectal, nasal, pulmonary, transdermal, vaginal, ocular, and the like (Eppstein (1988), supra; Siddiqui et al. (1987), supra; Banga et al. (1988), supra; Sanders (1990), supra; Verhoef (1990), supra; Barry, in *Delivery Systems for Peptide Drugs*, Davis et al., eds., Plenum Press: New York (1986), pp. 265-275; and Patton et al., *Adv. Drug Delivery Rev*, 8: 179-196 (1992)). With any of these routes, or, indeed, with any other route of administration or application, a protein or peptide drug, such as a griffithsin or conjugate thereof, may initiate an immunogenic reaction. In such situations it may be necessary to modify the molecule in order to mask immunogenic groups. It also can be possible to protect against undesired immune responses by judicious choice of method of formulation and/or administration. For example, site-specific delivery can be employed, as well as masking of recognition sites from the immune system by use or attachment of a so-called tolerogen, such as polyethylene glycol, dextran, albumin, and the like (Abuchowski et al. (1981), supra; Abuchowski et al., *J. Biol. Chem.*, 252: 3578-3581 (1977); Lisi et al., *J. Appl. Biochem*, 4: 19-33 (1982); and Wileman et al., *J. Pharm. Pharmacol*, 38: 264-271 (1986)). Such modifications also can have advantageous effects on stability and half-life both in vivo and ex vivo.

Procedures for covalent attachment of molecules, such as polyethylene glycol, dextran, albumin and the like, to proteins, such as griffithsins or conjugates thereof, are well-known to those skilled in the art, and are extensively documented in the literature (e.g., see Davis et al., in *Peptide and Protein Drug Delivery*, Lee, ed., Marcel Dekker: New York (1991), pp. 831-864).

Other strategies to avoid untoward immune reactions also can include the induction of tolerance by administration initially of only low doses. In any event, it will be apparent from the present disclosure to one skilled in the art that for any particular desired medical application or use of a griffithsin or conjugate thereof, the skilled artisan can select from any of a wide variety of possible compositions, routes of administration, or sites of application, what is advantageous.

Accordingly, the anti-viral griffithsins and conjugates thereof of the invention can be formulated into various compositions for use, for example, either in therapeutic treatment methods for infected individuals, or in prophylactic methods against viral, e.g., HIV and influenza virus, infection of uninfected individuals.

The invention also provides a composition, such as a pharmaceutical composition, which comprises an isolated and purified griffithsin, a griffithsin conjugate, a matrix-anchored griffithsin or a matrix-anchored griffithsin conjugate, such as an anti-viral effective amount thereof. The composition can further comprise a carrier, such as a pharmaceutically acceptable carrier. The composition can further comprise at least one additional anti-viral compound other than a griffithsin or conjugate thereof, such as in an anti-viral effective amount of an anti-viral compound. Suitable anti-viral compounds include cyanovirin, AZT, ddI, ddC, gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, neuroamidase inhibitors, amantatadine, rimantadine, enfurtide, and gramicidin. If the composition is to be used to induce an immune response, it comprises an immune response-inducing amount of a griffithsin or conjugate thereof and can further comprise an immunoadjuvant, such as polyphosphazene polyelectrolyte. The griffithsin used in the composition, e.g., pharmaceutical composition, can be isolated and purified from nature or genetically engineered. Similarly, the griffithsin conjugate can be genetically engineered or chemically coupled.

The inventive compositions can be administered to a host, such as a human, so as to inhibit viral infection in a prophylactic or therapeutic method. The compositions of the invention are particularly useful in inhibiting the growth or replication of a virus, such as influenza virus or a retrovirus, in particular an influenza virus or an immunodeficiency virus, such as HIV, specifically HIV-1 and HIV-2, inhibiting infectivity of the virus, inhibiting the binding of virus to a host cell, and the like. The compositions are useful in the therapeutic or prophylactic treatment of animals, such as humans, who are infected with a virus or who are at risk for viral infection, respectively. The compositions also can be used to treat objects or materials, such as medical equipment, supplies, or fluids, including biological fluids, such as blood, blood products and vaccine formulations, cells, tissues and organs, to remove or inactivate virus in an effort to prevent or treat viral infection of an animal, such as a human. Such compositions also are useful to prevent sexual transmission of viral infections, e.g., HIV, which is the primary way in which the world's AIDS cases are contracted (Merson (1993), supra). Adherence of the inventive anti-viral polypeptide or conjugate thereof to a solid support, such as a filter, can be used in clinics to remove all or part of the viral content of a biological solution. For example, filters comprising the inventive antiviral agents can be used to treat blood supplies prior to transfusion to reduce the risk of viral transmission. Such filters would find particular utility in clinics wherein risk of viral infection is high. It will be appreciated that total removal of the viral content of a biological solution is not required to achieve a beneficial effect. Removal of even a fraction of virus from a biological solution decreases the risk of infection of a patient.

Potential virucides used or being considered for use against sexual transmission of HIV are very limited; present agents in this category include, for example, nonoxynol-9 (Bird, *AIDS*, 5: 791-796 (1991)), gossypol and derivatives (Polsky et al., *Contraception*, 39: 579-587 (1989); Lin, *Antimicrob. Agents Chemother*, 33: 2149-2151 (1989); and Royer, *Pharmacol. Res*, 24: 407-412 (1991)), and gramicidin (Bourinbair, *Life Sci./Pharmacol. Lett*, 54: PL5-9 (1994); and Bourinbair et al., *Contraception*, 49: 131-137 (1994)). The method of prevention of sexual transmission of viral infection, e.g., HIV infection, in accordance with the invention comprises vaginal, rectal, oral, penile or other topical treatment with an anti-viral effective amount of a griffithsin and/or griffithsin conjugate, alone or in combination with another anti-viral compound as described herein.

In a novel approach to anti-HIV prophylaxis pursued under auspices of the U.S. National Institute of Allergy and Infectious Diseases (NIAID) (e.g., as conveyed by Painter, USA Today, Feb. 13, 1996), vaginal suppository instillation of live cultures of lactobacilli was being evaluated in a 900-woman study. This study was based especially upon observations of anti-HIV effects of certain $H_2O_2$-producing lactobacilli in vitro (e.g., see published abstract by Hilier, from NIAID-sponsored Conference on "Advances in AIDS Vaccine Development," Bethesda, Md., Feb. 11-15, 1996). Lactobacilli readily populate the vagina, and indeed are a predominant bacterial population in most healthy women (Redondo-Lopez et al., *Rev. Infect. Dis.*, 12: 856-872 (1990); Reid et al., *Clin. Microbiol. Rev.*, 3: 335-344 (1990); Bruce and Reid, *Can. J. Microbiol.*, 34: 339-343 (1988); Reu et al., *J. Infect. Dis.*, 171: 1237-1243 (1995); Hilier et al., *Clin. Infect. Dis.*, 16 (Suppl 4): S273-S281; and Agnew et al., *Sex. Transm. Dis.*, 22: 269-273 (1995)). Lactobacilli are also prominent, nonpathogenic inhabitants of other body cavities such as the mouth, nasopharynx, upper and lower gastrointestinal tracts, and rectum.

It is well-established that lactobacilli can be readily transduced using available genetic engineering techniques to incorporate a desired foreign DNA coding sequence, and that such lactobacilli can be made to express a corresponding desired foreign protein (see, e.g., Hols et al., *Appl. and Environ. Microbiol.*, 60: 1401-1413 (1994)). Therefore, within the context of the present disclosure, it will be appreciated by one skilled in the art that viable host cells containing a DNA sequence or vector of the invention, and expressing a polypeptide or fusion protein of the invention, can be used directly as the delivery vehicle for a griffithsin or fusion protein thereof to the desired site(s) in vivo. Preferred host cells for such delivery of griffithsins or fusion proteins thereof directly to desired site(s), such as, for example, to a selected body cavity, can comprise bacteria or yeast. More specifically, such host cells can comprise suitably engineered strain(s) of lactobacilli, enterococci, or other common bacteria, such as *E. coli*, normal strains of which are known to commonly populate body cavities. More specifically yet, such host cells can comprise one or more selected nonpathogenic strains of lactobacilli, such as those described by Andreu et al. ((1995), supra), especially those having high adherence properties to epithelial cells, such as, for example, adherence to vaginal epithelial cells, and suitably transformed using the DNA sequences of the present invention.

As reviewed by McGroarty (*FEMS Immunol. Med. Microbiol.*, 6: 251-264 (1993)) the "probiotic" or direct therapeutic application of live bacteria, particularly bacteria that occur normally in nature, more particularly lactobacilli, for treatment or prophylaxis against pathogenic bacterial or yeast infections of the urogenital tract, in particular the female urogenital tract, is a well-established concept. Recently, the use of a conventional probiotic strategy, in particular the use of live lactobacilli, to inhibit sexual transmission of HIV has been suggested, based specifically upon the normal, endogenous production of virucidal levels of $H_2O_2$ and/or lactic acid and/or other potentially virucidal substances by certain normal strains of lactobacilli (e.g., Hilier (1996), supra). However, the inventive use of non-mammalian cells, particularly bacteria, more particularly lactobacilli, specifically engineered with a foreign gene, more specifically a griffithsin gene, to express an anti-viral substance, more specifically a protein, and even more specifically a griffithsin, is heretofore unprecedented as a method of treatment of an animal, specifically a human, to prevent infection by a virus, specifically a retrovirus, more specifically HIV-1 or HIV-2.

Elmer et al. (*JAMA*, 275: 870-876 (1996)) have recently speculated that "genetic engineering offers the possibility of using microbes to deliver specific actions or products to the colon or other mucosal surfaces . . . other fertile areas for future study include defining the mechanisms of action of various biotherapeutic agents with the possibility of applying genetic engineering to enhance activities." Elmer et al. ((1996), supra) further point out that the terms "probiotic" and "biotherapeutic agent" have been used in the literature to describe microorganisms that have antagonistic activity toward pathogens in vivo; those authors more specifically prefer the term "biotherapeutic agent" to denote "microorganisms having specific therapeutic properties."

In view of the present disclosure, one skilled in the art will appreciate that the invention teaches an entirely novel type of "probiotic" or "biotherapeutic" treatment using specifically engineered strains of microorganisms provided herein which do not occur in nature. Nonetheless, available teachings concerning selection of optimal microbial strains, in particular bacterial strains, for conventional probiotic or biotherapeutic applications can be employed in the context of the invention. For example, selection of optimal *lactobacillus* strains for genetic engineering, transformation, direct expression of griffithsins or conjugates thereof, and direct probiotic or biotherapeutic applications, to treat or prevent viral (e.g., HIV) infection, can be based upon the same or similar criteria, such as those described by Elmer et al. ((1996), supra), typically used to select normal, endogenous or "nonengineered" bacterial strains for conventional probiotic or biotherapeutic therapy. Furthermore, the recommendations and characteristics taught by McGroarty, particularly for selection of optimal *lactobacillus* strains for conventional probiotic use against female urogenital infections, are pertinent to the present invention: " . . . lactobacilli chosen for incorporation into probiotic preparations should be easy and, if possible, inexpensive to cultivate . . . strains should be stable, retain viability following freeze-drying and, of course, be non-pathogenic to the host . . . it is essential that lactobacilli chosen for use in probiotic preparations should adhere well to the vaginal epithelium . . . ideally, artificially implanted lactobacilli should adhere to the vaginal epithelium, integrate with the indigenous microorganisms present, and proliferate" (McGroarty (1993), supra). While McGroarty's teachings specifically address selections of "normal" *lactobacillus* strains for probiotic uses against pathogenic bacterial or yeast infections of the female urogenital tract, similar considerations will apply to the selection of optimal bacterial strains for genetic engineering and "probiotic" or "biotherapeutic" application against viral infections as particularly encompassed by the present invention.

Accordingly, the method of the invention for the prevention of sexual transmission of viral infection, e.g., HIV infection, comprises vaginal, rectal, oral, penile, or other topical, insertional, or instillational treatment with an anti-viral effective amount of a griffithsin, a griffithsin conjugate or fusion protein, a matrix-anchored griffithsin or conjugate or fusion protein thereof, and/or viable host cells transformed to express a griffithsin or conjugate or fusion protein thereof, alone or in combination with one or more other anti-viral compound (e.g., as described above). However, commensal organisms which produce griffithsin or a fragment, homolog, or conjugate thereof can inhibit viruses other than HIV. For example, commensal microorganisms that produce the inventive polypeptide can be instilled in mucosal tissue at the site of influenza contact, such as nasal or oral mucosa, to inhibit influenza infection of a host.

Compositions for use in the prophylactic or therapeutic treatment methods of the invention comprise one or more griffithsin(s) or conjugate(s) or fusion protein(s) thereof, either one of which can be matrix-anchored, and desirably a carrier therefor, such as a pharmaceutically acceptable carrier. Pharmaceutically acceptable carriers are well-known to those who are skilled in the art, as are suitable methods of administration. The choice of carrier will be determined in part by the particular griffithsin or conjugate or fusion protein thereof, as well as by the particular method used to administer the composition.

One skilled in the art will appreciate that various routes of administering a drug are available, and, although more than one route can be used to administer a particular drug, a particular route can provide a more immediate and more effective reaction than another route. For example, the anti-viral agent of the invention can be inhaled in methods of prophylactically treating a subject for influenza infection. Delivery of the anti-viral agent to a location of initial viral contact, such as the nose or mouth, blocks the onset of infection. The anti-viral agent can be administered via subcutaneous injection. Alternatively, in acute or critical medical situations, the anti-viral agent can be administered intravenously. In many cases of infection, a patient generates an immune response to a virus. However, the effects of the viral infection so severely compromise the health of the patient that an effective immune response is not reached prior to death. Administration of the anti-viral agent can prolong the life of the patient until a patient's natural immune defense clears the virus. Furthermore, one skilled in the art will appreciate that the particular pharmaceutical carrier employed will depend, in part, upon the particular griffithsin or conjugate or fusion protein thereof employed, and the chosen route of administration. Accordingly, there is a wide variety of suitable formulations of the composition of the invention.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., *Science*, 260: 912-915 (1993)).

The anti-viral agent of the invention (e.g., griffithsin or conjugates thereof), alone or in combination with other anti-viral compounds, can be made into aerosol formulations or microparticulate powder formulations to be administered via inhalation. These aerosol formulations can be placed into pressurized acceptable propellants, such as dichlorodifluoromethane, propane, nitrogen, and the like.

The anti-viral agent of the invention (e.g., griffithsin or conjugates thereof), alone or in combinations with other anti-viral compounds or absorption modulators, can be made into suitable formulations for transdermal application and absorption, such as a patch (Wallace et al. (1993), supra). Transdermal electroporation or iontophoresis also can be used to promote and/or control the systemic delivery of the compounds and/or compositions of the present invention through the skin (e.g., see Theiss et al., *Meth. Find. Exp. Clin. Pharmacol.*, 13: 353-359 (1991)).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such as, for example, freeze-dried lactobacilli or live *lactobacillus* cultures genetically engineered to directly produce a griffithsin or conjugate or fusion protein thereof of the present invention, such carriers as are known in the art. Topical administration is preferred for the prophylactic and therapeutic treatment of influenza viral infection, such as through the use of an inhaler, for example.

Formulations for rectal administration can be presented as a suppository with a suitable base comprising, for example, cocoa butter or a salicylate. Formulations suitable for vaginal administration can be presented as pessaries, tampons, creams, gels, pastes, foams, or spray formulas containing, in addition to the active ingredient, such as, for example, freeze-dried lactobacilli or live *lactobacillus* cultures genetically engineered to directly produce a griffithsin or conjugate or fusion protein thereof of the present invention, such carriers as are known in the art to be appropriate. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, and a sponge.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising a griffithsin or griffithsin conjugate suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations. Preferably, the griffithsin is produced by recombinant DNA technology. The griffithsin conjugate can be produced by recombinant DNA technology or by chemical coupling of a griffithsin with an effector molecule as described above. Similarly, formulations suitable for ex vivo sterilization, inactivation, or removal of virus, such as infectious virus, from a sample, such as blood, blood products, sperm, or other bodily products, such as a fluid, cells, a tissue or an organ, or any other solution, suspension, emulsion, vaccine formulation (such as in the removal of infectious virus), or any other material which can be administered to a patient in a medical procedure, can be selected or adapted as appropriate by one skilled in the art, from any of the aforementioned compositions or formulations. However, suitable formulations for ex vivo sterilization or inactivation or removal of virus from a sample or on an inanimate object are by no means limited to any of the aforementioned formulations or compositions. For example, such formulations or compositions can comprise a functional griffithsin, such as that which is encoded by SEQ ID NO:3, or anti-viral fragment thereof, such as a fragment comprising at least eight contiguous amino acids of SEQ ID NO:3, wherein the at least eight contiguous amino acids bind to a virus, or a conjugate or fusion protein of either of the foregoing, attached to a solid support matrix, to facilitate contacting or binding infectious virus in a sample or removing infectious virus from a sample as described above, e.g., a bodily product such as a fluid, cells, a tissue or an organ from an organism, in particular a mammal, such as a human, including, for example, blood, a component of blood (e.g., plasma, blood cells, and the like), or sperm. Preferably, the anti-viral polypeptide comprises SEQ ID NO:3. Also preferably, the at least eight contiguous amino acids bind gp120 of HIV, in particular infectious HIV. As a more specific example, such a formulation or composition can comprise a functional griffithsin, or conjugate or fusion protein thereof, attached to (e.g., coupled to or immobilized on) a solid support matrix comprising magnetic beads, to facilitate contacting, binding and removal of infectious virus, and to enable magnet-assisted removal of the virus from a sample as described above, e.g., a bodily product such as a fluid, cells, a tissue or an organ, e.g., blood, a component of blood, or sperm. Alternatively, and also preferably, the solid support matrix comprises a contraceptive device, such as a condom, a diaphragm, a cervical cap, a vaginal ring, or a sponge. The anti-viral agent also can be encapsulated or dispersed within a solid matrix, such as a vaginal ring or sponge. Methods for encapsulating biotherapeutics into, for example, biocompatible sustained release devices, are known in the art.

As an even more specific illustration, such a composition (e.g., for ex vivo) can comprise a functional (e.g., gp120-binding, HIV-inactivating) griffithsin, or conjugate or fusion protein thereof, attached to a solid support matrix, such as magnetic beads or a flow-through matrix, by means of an anti-griffithsin antibody or at least one effector component, which can be the same or different, such as polyethylene glycol, albumin, or dextran. The conjugate can further comprise at least one effector component, which can be the same or different, selected from the group consisting of, for example, an immunological reagent and a toxin. A flow-through matrix would comprise, for instance, a configuration similar to an affinity column. The griffithsin can be covalently coupled to a solid support matrix via an anti-griffithsin antibody, described below. Methods of attaching an antibody to a solid support matrix are well-known in the art (see, for example, Harlow and Lane. *Antibodies: A Laboratory Manual*, Cold Springs Harbor Laboratory: Cold Spring Harbor, N.Y. (1988)). Alternatively, the solid support matrix, such as magnetic beads, can be coated with streptavidin, in which case the griffithsin or fragment thereof (which comprises at least eight contiguous amino acids of SEQ ID NO:3 or SEQ ID NO:2), or a conjugate or fusion protein of either one, is biotinylated. The at least eight contiguous amino acids of SEQ ID NO:2 desirably have anti-viral activity and preferably bind gp120 of HIV, which preferably is infectious. Preferably, the anti-viral polypeptide comprises SEQ ID NO:3 or SEQ ID NO:2. Such a composition can be prepared, for example, by biotinylating the griffithsin, or conjugate or fusion protein thereof, and then contacting the biotinylated protein or peptide with a (commercially available) solid support matrix, such as magnetic beads, coated with streptavidin. The use of biotinylation as a means to attach a desired biologically active protein or peptide to a streptavidin-coated support matrix, such as magnetic beads, is well-known in the art.

One skilled in the art will appreciate that a suitable or appropriate formulation can be selected, adapted or developed based upon the particular application at hand.

For ex vivo uses, such as virucidal treatments of inanimate objects or materials, blood or blood products, or tissues, the amount of griffithsin, conjugate thereof, fusion protein thereof, or composition of any of the foregoing, to be employed should be sufficient that any virus or virus-producing cells present will be rendered noninfectious or will be destroyed. For example, for HIV, this would require that the virus and/or the virus-producing cells be exposed to concentrations of griffithsin in the range of 0.1-1000 nM. Similar considerations apply to in vivo applications. Therefore, the designation of "anti-viral effective amount" is used generally to describe the amount of a particular griffithsin, conjugate, fusion protein, or composition thereof required for anti-viral efficacy in any given application.

In view of the above, the invention also provides a method of inhibiting prophylactically or therapeutically a viral infection of a host in which an anti-viral effective amount of an above-described anti-viral polypeptide, conjugate, or fusion protein is administered to the host. Upon administration of the anti-viral effective amount of the anti-viral polypeptide, conjugate, or fusion protein, the viral infection is inhibited.

The invention additionally provides a method of prophylactically or therapeutically inhibiting a viral infection of a host in which an anti-viral effective amount of a composition comprising an isolated and purified anti-viral polypeptide, or anti-viral polypeptide conjugate or fusion protein, either one of which comprises at least eight contiguous amino acids of SEQ ID NO:3 having anti-viral activity, attached to or encapsulated within a solid support matrix is administered to the host. By "therapeutically" is meant that the host already has been infected with the virus. By "prophylactically" is meant that the host has not yet been infected with the virus but is at risk of being infected with the virus. Prophylactic treatment is intended to encompass any degree of inhibition of viral infection, including, but not limited to, complete inhibition, as one of ordinary skill in the art will readily appreciate that any degree in inhibition of viral infection is advantageous. Preferably, the inventive active agent is administered before viral infection or immediately upon determination of viral infection and is continuously administered until the virus is undetectable. The method optionally further comprises the prior, simultaneous or subsequent administration, by the same route or a different route, of an antiviral agent or another agent that is efficacious in inhibiting the viral infection. Upon administration of the anti-viral effective amount of the composition, the viral infection is inhibited. Preferably, the solid support matrix is a contraceptive device, such as a condom, diaphragm, cervical cap, vaginal ring, or sponge. In an alternative embodiment, a solid support matrix can be surgically implanted and later removed.

For in vivo uses, the dose of a griffithsin, or conjugate or composition thereof, administered to an animal, particularly a human, in the context of the invention should be sufficient to effect a prophylactic or therapeutic response in the individual over a reasonable time frame. The dose used to achieve a desired anti-viral concentration in vivo (e.g., 0.1-1000 nM) will be determined by the potency of the particular griffithsin or conjugate employed, the severity of the disease state of infected individuals, as well as, in the case of systemic administration, the body weight and age of the infected individual. The size of the dose also will be determined by the existence of any adverse side effects that may accompany the particular griffithsin, or conjugate or composition thereof, employed. It is always desirable, whenever possible, to keep adverse side effects to a minimum.

The invention also provides a method of removing virus, such as infectious virus, from a sample. The method comprises contacting the sample with a composition comprising an isolated and purified anti-viral polypeptide or conjugate or fusion protein thereof, comprising at least eight contiguous amino acids of SEQ ID NO:3 (or SEQ ID NO: 2). The at least eight contiguous amino acids desirably have anti-viral activity and bind to the virus and the anti-viral polypeptide (or conjugate or fusion protein of either of the foregoing) is attached to a solid support matrix, such as a magnetic bead. "Attached" is used herein to refer to attachment to (or coupling to) and immobilization in or on a solid support matrix. While any means of attachment can be used, preferably, attachment is by covalent bonds. The method further comprises separating the sample and the composition by any suitable means, whereupon the virus, such as infectious virus, is removed from the sample. Preferably, the anti-viral polypeptide comprises SEQ ID NO:3 (or SEQ ID NO:2). In one embodiment, the anti-viral polypeptide is conjugated with an anti-griffithsin antibody or at least one effector component, which can be the same or different, selected from polyethylene glycol, dextran and albumin, in which case the anti-viral polypeptide is desirably attached to the solid support matrix through at least one effector component. The anti-viral polypeptide can be further conjugated with at least one effector component, which can be the same or different, selected from the group consisting of an immunological reagent and a toxin. In another embodiment, the solid support matrix is coated with streptavidin and the anti-viral polypeptide is biotinylated. Through biotin, the biotinylated anti-viral polypeptide is attached to the streptavidin-coated solid support matrix. Other types of means, as are known in the art, can be used to attach a functional griffithsin (i.e., an anti-viral polypeptide or conjugate as described above) to a solid support matrix, such as a magnetic bead, in which case contact with a magnet is used to separate the sample and the composition. Similarly, other types of solid support matrices can be used, such as a matrix comprising a porous surface or membrane, over or through which a sample is flowed or percolated, thereby selectively entrapping or removing infectious virus from the sample. The choice of solid support matrix, means of attachment of the functional griffithsin to the solid support matrix, and means of separating the sample and the matrix-anchored griffithsin will depend, in part, on the sample (e.g., fluid vs. tissue) and the virus to be removed. It is expected that the use of a selected coupling molecule can confer certain desired properties to a matrix, comprising a functional griffithsin coupled therewith, that may have particularly advantageous properties in a given situation. Preferably, the sample is blood, a component of blood, sperm, cells, tissue or an organ. Also, preferably the sample is a vaccine formulation, in which case the virus that is removed is infectious, such as HIV, although HIV, in particular infectious HIV, can be removed from other samples in accordance with this method.

For instance, the skilled practitioner might select a poly(ethylene glycol) molecule for attaching a functional griffithsin to a solid support matrix, thereby to provide a matrix-anchored griffithsin, wherein the griffithsin is attached to the matrix by a longer "tether" than would be feasible or possible for other attachment methods, such as biotinylation/streptavidin coupling. A griffithsin coupled by a poly(ethylene glycol) "tether" to a solid support matrix (such as magnetic beads, porous surface or membrane, and the like) can permit optimal exposure of a binding surface, epitope, hydrophobic or electrophilic focus, and/or the like, on a functional griffithsin in a manner that, in a given situation and/or for a particular virus, facilitates the binding and/or inactivation of the virus. A preferred solid support matrix is a magnetic bead such that separation of the sample and the composition is effected by a magnet. In a preferred embodiment of the method, the at least eight contiguous amino acids bind gp120 of HIV and HIV is removed from the sample.

Similarly, other types of solid support matrices can be used, such as a matrix comprising a porous surface or membrane, over or through which a sample is flowed or percolated, thereby selectively inhibiting infectious virus (e.g., HIV or influenza) in the sample. The choice of solid support matrix, means of attachment of the functional griffithsin to the solid support matrix, and means of separating the sample and the matrix-anchored griffithsin will depend, in part, on the sample (e.g., fluid vs. tissue) and the virus to be inhibited. It is expected that the use of a selected coupling molecule can confer certain desired properties to a matrix, comprising a functional griffithsin coupled therewith, that may have particularly advantageous properties in a given situation.

The methods described herein also have utility in real time ex vivo inhibition of virus or virus infected cells in a bodily fluid, such as blood, e.g., in the treatment of viral infection, or in the inhibition of virus in blood or a component of blood, e.g., for transfusion, in the inhibition or prevention of viral infection. Such methods also have potential utility in dialysis, such as kidney dialysis, and in inhibiting virus in sperm obtained from a donor for in vitro and in vivo fertilization. The methods also have applicability in the context of tissue and organ transplantations.

In summary, a griffithsin attached to a solid support matrix, such as a magnetic bead, can be used to remove virus, in particular infectious virus, including immunodeficiency virus, such as HIV, e.g., HIV-1 or HIV-2, from a sample, such as a sample comprising both infectious and noninfectious virus. The inventive method also can be used to remove viral glycoprotein presenting cells, e.g., infected cells that have, for example, gp120 on their surfaces, from a sample.

The invention, therefore, further provides a composition comprising naturally-occurring, non-infectious virus, such as a composition produced as described above. The composition can further comprise a carrier, such as a biologically or pharmaceutically acceptable carrier, and an immuno-adjuvant. Preferably, the noninfectious virus is an influenza or an immunodeficiency virus, such as HIV, e.g., HIV-1 or HIV-2. Alternatively, and also preferably, the noninfectious virus is FIV. A composition comprising only naturally-occurring, non-infectious virus has many applications in research and the prophylactic treatment of a viral infection. In terms of prophylactic treatment of a viral infection, the skilled artisan will appreciate the need to eliminate completely all infectious virus from the composition. If desired, further treatment of the composition comprising non-infectious particles with virus-inactivating chemicals, such as imines or psoralens, and/or pressure or heat inactivation, will further the non-infectious nature of the composition. For example, an immune response-inducing amount of the inventive composition can be administered to an animal at risk for a viral infection in order to induce an immune response. The skilled artisan will appreciate that such a composition is a significant improvement over previously disclosed compositions in that the virus is non-infectious and naturally-occurring. Thus, there is no risk of inadvertent infection, greater doses can be administered in comparison to compositions comprising infectious viral particles, and the subsequent immune response will assuredly be directed to antigens present on naturally-occurring virus. The composition comprising naturally-occurring, non-infectious virus can be administered in any manner appropriate to induce an immune response. Preferably, the virus is administered, for example, intramuscularly, mucosally, intravenously, subcutaneously, or topically. Preferably, the composition comprises naturally-occurring, non-infectious human immunodeficiency virus comprising gp120.

The composition comprising naturally-occurring, non-infectious virus can be combined with various carriers, adjuvants, diluents or other anti-viral therapeutics, if desired. Appropriate carriers include, for example, ovalbumin, albumin, globulins, hemocyanins, and the like. Adjuvants or immuno-adjuvants are incorporated in most cases to stimulate further the immune system. Any physiologically appropriate adjuvant can be used. Suitable adjuvants for inclusion in the inventive composition include, for example, aluminum hydroxide, beryllium sulfate, silica, kaolin, carbon, bacterial endotoxin, saponin, and the like.

Thus, the invention also provides a method of inducing an immune response to a virus in an animal. The method comprises administering to the animal an immune response-inducing amount of a composition comprising naturally-occurring, non-infectious virus as described above.

The appropriate dose of a composition comprising naturally-occurring, non-infectious virus required to induce an immune response to the virus in an animal is dependent on numerous factors, such as size of the animal and immune competency. The amount of composition administered should be sufficient to induce a humoral and/or cellular immune response. The amount of non-infectious virus in a particular composition can be determined using routine methods in the art, such as the Coulter HIV p24 antigen assay (Coulter Corp., Hialeah, Fla.). Any suitable dose of a composition comprising non-infectious virus is appropriate so long as an immune response is induced, desirably without the appearance of harmful side effects to the host. In this regard, compositions comprising from about $10^1$ to about $10^5$ particles, preferably from about $10^2$ to about $10^4$ particles, most preferably about $10^3$ particles, are suitable for inducing an immune response.

One of ordinary skill can determine the effectiveness of the composition to induce an immune response using routine methods known in the art. Cell-mediated response can be determined by employing, for example, a virus antigen-stimulated T-cell proliferation assay. The presence of a humoral immune response can be determined, for instance, with the Enzyme Linked Immunosorbent Assay (ELISA). The skilled artisan will appreciate that there are numerous other suitable assays for evaluating induction of an immune response. To the extent that a dose is inadequate to induce an appropriate immune response, "booster" administrations can subsequently be administered in order to prompt a more effective immune response.

In terms of administration of the inventive anti-viral agents or conjugates thereof, the dosage can be in unit dosage form, such as a tablet or capsule. The term "unit dosage form" as used herein refers to physically discrete units suitable as unitary dosages for human and animal subjects, each unit containing a predetermined quantity of a griffithsin or conjugate thereof, alone or in combination with other anti-viral agents, calculated in an amount sufficient to produce the desired effect in association with a pharmaceutically acceptable diluent, carrier, or vehicle.

The specifications for the unit dosage forms of the invention depend on the particular griffithsin, or conjugate or composition thereof, employed and the effect to be achieved, as well as the pharmacodynamics associated with each griffithsin, or conjugate or composition thereof, in the host. The dose administered should be an "anti-viral effective amount" or an amount necessary to achieve an "effective level" in the individual patient.

Since the "effective level" is used as the preferred endpoint for dosing, the actual dose and schedule can vary, depending upon interindividual differences in pharmacokinetics, drug distribution, and metabolism. The "effective level" can be defined, for example, as the blood or tissue level (e.g., 0.1-1000 nM) desired in the patient that corresponds to a concentration of one or more griffithsin or conjugate thereof, which inhibits a virus, such as HIV, in an assay known to predict for clinical anti-viral activity of chemical compounds and biological agents. The "effective level" for agents of the invention also can vary when the griffithsin, or conjugate or composition thereof, is used in combination with AZT or other known anti-viral compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the invention by a direct (e.g., analytical chemical analysis) or indirect (e.g., with surrogate indicators such as p24 or RT) analysis of appropriate patient samples (e.g., blood and/or tissues).

In the treatment of some virally infected individuals, it can be desirable to utilize a "mega-dosing" regimen, wherein a large dose of the griffithsin or conjugate thereof is administered, time is allowed for the drug to act, and then a suitable reagent is administered to the individual to inactivate the drug.

The pharmaceutical composition can contain other pharmaceuticals, in conjunction with the griffithsin or conjugate thereof, when used to therapeutically treat a viral infection, such as an influenza infection or an HIV infection which results in AIDS. Representative examples of these additional pharmaceuticals include anti-viral compounds, virucides, immunomodulators, immunostimulants, antibiotics and absorption enhancers. Exemplary anti-viral compounds include cyanovirin, AZT, ddI, ddC, gancylclovir, fluorinated dideoxynucleosides, nonnucleoside analog compounds, such as nevirapine (Shih et al., *PNAS*, 88: 9878-9882 (1991)), TIBO derivatives, such as R82913 (White et al., *Anti-viral Res.*, 16: 257-266 (1991)), BI-RJ-70 (Merigan, *Am. J. Med.*, 90 (Suppl. 4A):8S-17S (1991)), michellamines (Boyd et al., *J. Med. Chem.*, 37: 1740-1745 (1994)) and calanolides Kashman et al., *J. Med. Chem.*, 35: 2735-2743 (1992)), nonoxynol-9, gossypol and derivatives, gramicidin (Bourinbair et al. (1994), supra), neuraminidase inhibitors, amantadine, enfurtide, and the like. Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneutnoeystitis carnii* agents. Exemplary absorption enhancers include bile salts and other surfactants, saponins, cyclodextrins, and phospholipids (Davis (1992), supra).

Administration of a griffithsin or conjugate or fusion protein thereof with other anti-retroviral agents and particularly with known RT inhibitors, such as ddC, AZT, ddI, ddA, or other inhibitors that act against other HIV proteins, such as anti-TAT agents, is expected to inhibit most or all replicative stages of the viral life cycle. The dosages of ddC and AZT used in AIDS or ARC patients have been published. A virustatic range of ddC is generally between 0.05 μM to 1.0 μM. A range of about 0.005-0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently, 0.01 mg/kg body weight ddC given every 8 hrs is preferred. When given in combined therapy, the other anti-viral compound, for example, can be given at the same time as the griffithsin or conjugate thereof or the dosing can be staggered as desired. The two drugs also can be combined in a composition. Doses of each can be less when used in combination than when either is used alone.

It will also be appreciated by one skilled in the art that a DNA sequence of a griffithsin or conjugate thereof of the invention can be inserted ex vivo into mammalian cells previously removed from a given animal, in particular a human, host. Such cells can be employed to express the corresponding griffithsin or conjugate or fusion protein in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al. (1994), supra). It is also possible that, as an alternative to ex vivo insertion of the DNA sequences of the invention, such sequences can be inserted into cells directly in vivo, such as by use of an appropriate viral vector. Such cells transfected in vivo are expected to produce anti-viral amounts of griffithsin or a conjugate or fusion protein thereof directly in vivo.

Given the present disclosure, it will be additionally appreciated that a DNA sequence corresponding to a griffithsin or conjugate thereof can be inserted into suitable nonmammalian host cells, and that such host cells will express therapeutic or prophylactic amounts of a griffithsin or conjugate or fusion protein thereof directly in vivo within a desired body compartment of an animal, in particular a human. Example 5 illustrates the transformation and expression of effective virucidal amounts of a griffithsin in a non-mammalian cell, more specifically a bacterial cell. In a preferred embodiment of the invention, a method of female-controllable prophylaxis against HIV infection comprises the intravaginal administration and/or establishment of, in a female human, a persistent intravaginal population of lactobacilli that have been transformed with a coding sequence of the invention to produce, over a prolonged time, effective virucidal levels of a griffithsin or conjugate thereof, directly on or within the vaginal and/or cervical and/or uterine mucosa. It is noteworthy that both the World Health Organization (WHO), as well as the U.S. National Institute of Allergy and Infectious Diseases, have pointed to the need for development of female-controlled topical microbicides, suitable for blocking the transmission of HIV, as an urgent global priority (Lange et al., *Lancet*, 341: 1356 (1993); Fauci, *NIAID News*, Apr. 27, 1995). A composition comprising the inventive anti-viral agent and a solid-support matrix is particularly useful in this regard, particularly when the solid-support matrix is a contraceptive device, such as a condom, a diaphragm, a cervical cap, a vaginal ring, or a sponge. In another embodiment, a colony of commensal organisms transduced with the nucleic acid of the invention and producing the inventive anti-viral agent is applied to mucosal tissue associated with the onset of influenza infection, such as respiratory or oral mucosal.

The invention also provides antibodies directed to the polypeptides of the invention. The availability of antibodies to any given protein is highly advantageous, as it provides the basis for a wide variety of qualitative and quantitative analytical methods, separation and purification methods, and other useful applications directed to the subject polypeptides. Accordingly, given the present disclosure and the polypeptides of the invention, it will be readily apparent to one skilled in the art that antibodies, in particular antibodies specifically binding to a polypeptide of the invention, can be prepared using well-established methodologies (e.g., such as the methodologies described in detail by Harlow and Lane, in *Antibodies. A Laboratory Manual*, Cold Spring Harbor Laboratory, Cold Spring Harbor (1988), pp. 1-725). Such antibodies can comprise both polyclonal and monoclonal antibodies. Furthermore, such antibodies can be obtained and employed either in solution-phase or coupled to a desired solid-phase matrix, such as magnetic beads or a flow through matrix. Having in hand such antibodies as provided by the invention, one skilled in the art will further appreciate that such antibodies, in conjunction with well-established procedures (e.g., such as described by Harlow and Lane (1988), supra) comprise useful methods for the detection, quantification, or purification of a griffithsin, conjugate thereof, or host cell transformed to produce a griffithsin or conjugate or fusion protein thereof. Example 6 further illustrates an antibody that specifically binds to a griffithsin. Accordingly, the invention further provides a composition comprising an anti-griffithsin antibody bound to the anti-viral agent of the invention, preferably an anti-viral polypeptide comprising at least eight contiguous amino acids of SEQ ID NO:3.

Matrix-anchored anti-griffithsin antibodies also can be used in a method to remove virus in a sample. Preferably, the antibody binds to an epitope of an anti-viral polypeptide of SEQ ID NO:2 or SEQ ID NO:3. Preferably, the matrix is a solid support matrix, such as a magnetic bead or a flow-through matrix. If the solid support matrix to which the anti-griffithsin antibody is attached comprises magnetic beads, removal of the antibody-griffithsin-virus complex can be readily accomplished using a magnet.

In view of the above, the invention provides a method of removing virus from a sample. The method comprises (a) contacting the sample with a composition comprising an isolated and purified anti-viral polypeptide or conjugate or fusion protein thereof, wherein (i) the anti-viral polypeptide comprises at least eight contiguous amino acids of SEQ ID NO: 3, and (ii) the at least eight contiguous amino acids bind to the virus, and (b) contacting the sample with an anti-griffithsin antibody attached to a solid support matrix, whereupon the anti-griffithsin antibody binds to the anti-viral polypeptide or conjugate or fusion protein thereof to which is bound the virus, and (c) separating the solid support matrix from the sample, whereupon the virus is removed from the sample. Preferably, the anti-viral polypeptide comprises SEQ ID NO:3. Desirably, the virus that is removed is infectious, such as HIV. The sample can be blood, a component of blood, sperm, cells, tissue or an organ.

The antibody for use in the aforementioned method is an antibody that binds to a polypeptide comprising at least eight contiguous amino acids of SEQ ID NO:3, and, which polypeptide can bind to and inactivate a virus. The antibody can be coupled to the solid support matrix using similar methods and with similar considerations as described above for attaching a griffithsin to a solid support matrix. For example, coupling methods and molecules employed to attach an anti-griffithsin antibody to a solid support matrix, such as magnetic beads or a flow-through matrix, can employ biotin/streptavidin coupling or coupling through molecules, such as polyethylene glycol, albumin or dextran. Also analogously, it can be shown that, after such coupling, the matrix-anchored anti-griffithsin antibody retains its ability to bind to a polypeptide comprising at least eight contiguous amino acids of SEQ ID NO:3, which polypeptide can bind to and inactivate a virus.

The invention also provides an anti-griffithsin antibody that is anti-idiotypic in respect to a viral glycoprotein, such as gp120, i.e., has an internal image of gp120 of a primate immunodeficiency virus. Preferably, the antibody can compete with gp120 of a primate immunodeficiency virus for binding to a griffithsin. In this regard, the primary immunodeficiency virus preferably is HIV-1 or HIV-2 and the griffithsin preferably consists essentially of SEQ ID NO:2 or SEQ ID NO:3. Anti-idiotypic antibodies can be generated in accordance with methods known in the art (see, for example, Benjamin, in *Immunology: a short course*, Wiley-Liss, N Y (1996), pp. 436-437; Kuby, in *Immunology,* 3rd ed., Freeman, N.Y. (1997), pp. 455-456; Greenspan et al., *FASEB J.,* 7: 437-443 (1993); and Poskitt, *Vaccine,* 9: 792-796 (1991)). Such an anti-idiotypic (in respect to gp120) anti-griffithsin antibody is useful in a method of inhibiting infection of an animal with a virus as provided herein.

In view of the above, a griffithsin can be administered to an animal, the animal generates anti-griffithsin antibodies, among which are antibodies that have an internal image of a viral glycoprotein, such as gp120. In accordance with well-known methods, polyclonal or monoclonal antibodies can be obtained, isolated, and selected. Selection of an anti-griffithsin antibody that has an internal image of gp120 can be based upon competition between the anti-griffithsin antibody and gp120 for binding to a griffithsin, or upon the ability of the anti-griffithsin antibody to bind to a free griffithsin as opposed to a griffithsin bound to gp120. Such an anti-griffithsin antibody can be administered to an animal to inhibit a viral infection in accordance with methods provided herein. Although nonhuman anti-idiotypic antibodies, such as an anti-griffithsin antibody that has an internal image of gp120 and, therefore, is anti-idiotypic to gp120, are proving useful as vaccine antigens in humans, their favorable properties might, in certain instances, be further enhanced and/or their adverse properties further diminished, through “humanization” strategies, such as those recently reviewed by Vaughan (*Nature Biotech.,* 16: 535-539 (1998)). Alternatively, a griffithsin can be directly administered to an animal to inhibit a viral infection in accordance with methods provided herein such that the treated animal, itself, generates an anti-griffithsin antibody that has an internal image of gp120. The production of anti-idiotypic antibodies, such as anti-griffithsin antibody that has an internal image of gp120 and, therefore, is anti-idiotypic to gp120, in an animal to be treated is known as “anti-idiotype induction therapy,” and is described by Madiyalakan et al. (*Hybridoma,* 14: 199-203 (1995)), for example.

In view of the above, the invention enables another method of inhibiting infection of an animal, such as a mammal, in particular a human, with a virus. The method comprises administering to the animal an anti-griffithsin antibody, or a composition comprising same, in an amount sufficient to induce in the animal an immune response to the virus, whereupon the infection of the animal with the virus is inhibited. Preferably, the anti-griffithsin antibody has an internal image of a viral glycoprotein, such as gp120 of an immunodeficiency virus with which the animal can be infected, such as a primate immunodeficiency virus. Preferably, the antibody can compete with, for example, gp120 of a primate immunodeficiency virus for binding to a griffithsin. In this regard, the primate immunodeficiency virus preferably is HIV-1 or HIV-2 and the griffithsin preferably consists essentially of SEQ ID NO:3 or SEQ ID NO:2. The method can further comprise the administration of an immunostimulant.

Also enabled by the invention is yet another method of inhibiting infection of an animal, such as a mammal, in particular a human, with a virus. The method comprises administering to the animal a griffithsin, which binds a viral glycoprotein, such as gp120 of an immunodeficiency virus with which the animal can be infected, in an amount sufficient to induce in the animal an anti-griffithsin antibody in an amount sufficient to induce an immune response to a virus sufficient to inhibit infection of the animal with the virus. Preferably, the anti-griffithsin antibody has an internal image of gp120 of an immunodeficiency virus with which the animal can be infected, such as a primate immunodeficiency virus. Preferably, the antibody can compete with gp120 of a primate immunodeficiency virus for binding to a griffithsin. In this regard, the primate immunodeficiency virus preferably is HIV-1 or HIV-2 and the griffithsin preferably consists essentially of SEQ ID NO:2 or SEQ ID NO:3.

With respect to the above methods, sufficient amounts can be determined in accordance with methods known in the art. Similarly, the sufficiency of an immune response in the inhibition of a viral infection in an animal also can be assessed in accordance with methods known in the art.

Either one of the above methods can further comprise concurrent, pre- or post-treatment with an adjuvant to enhance the immune response, such as the prior, simultaneous or subsequent administration, by the same or a different route, of an antiviral agent or another agent that is efficacious in inducing an immune response to the virus, such as an immunostimulant. See, for example, Harlow et al. (1988), supra.

The inventive griffithsins, conjugates, host cells, antibodies, compositions and methods are further described in the context of the following examples. These examples serve to illustrate further the present invention and are not intended to limit the scope of the invention.

EXAMPLES

Example 1

This example illustrates a method of isolating and purifying griffithsin from Griffithsin sp. and elucidating the griffithsin amino acid sequence.

Anti-HIV bioassay guided fractionation was used to track the isolation of the griffithsin polypeptide. In brief, the cellular mass from *Griffithsia* sp. was harvested by filtration, freeze-dried, and extracted first with $H_2O$ followed by (1:1) $MeOH$-$CH_2Cl_2$. Individual aliquots of the organic and aqueous extracts were tested for cytoprotective properties in the NCI primary anti-HIV screen (Weislow et al. *J. Natl. Cancer Inst.*, 81: 577-586 (1989)). Only the $H_2O$ extract showed anti-HIV activity.

A freeze-dried aqueous extract (10 g) was brought to a concentration of 50 mg/ml by addition of $DDH_2O$ and maintained on ice. Crystalline ammonium sulfate (Sigma, St. Louis, Mo.; molecular biology grade) was added to the solution such that the final concentration of the mixture was 75% saturation. The mixture was allowed to precipitate on ice overnight, and was then centrifuged at 3000 rpm for 50 min. The resulting pellets were set aside. The supernatant was brought to 1 M ammonium sulfate followed by another round of precipitation and centrifugation. The pellets from the second centrifugation were saved, and the resulting supernatant was filtered using a 0.22 µm filter and subjected to hydrophobic interaction chromatography. A BioCad workstation (Perseptive Biosystems) was used for the following column chromatographies. The protein solution from the centrifugation and filtration steps was injected onto a Poros PE column (10×100 mm, Perseptive Biosystems) pre-equilibrated with a starting buffer of 50 mM sodium phosphate, 1.5 M ammonium sulfate, pH 7.5. The column was eluted at a flow rate of 15 ml/min over the following gradient: (1) 7 column volumes (CV, equal to 7.85 ml) of the starting buffer; (2) 1.5-0 M ammonium sulfate over 2 CV; (3) 0 M ammonium sulfate for 15 CV. The eluate was monitored for both conductivity and absorbance (280 nm). Ammonium sulfate was added to the void fraction possessing anti-HIV activity to bring the final concentration to 75% saturation. The mixture was allowed to precipitate on ice overnight, and was then centrifuged at 3000 rpm for 50 min. $DDH_2O$-resuspended pellets were first concentrated using a 10 kDa molecular weight limit membrane, dialyzed against 0.02% sodium azide, and then brought up to a concentration of 25 mM Tris-HCl, pH 8.5. The resulting protein solution was injected onto a Poros HQ anion exchange column (10×100 mm, Perseptive Biosystems) pre-equilibrated with a starting buffer of 25 mM Tris-HCl, pH 8.5. The column was eluted at a flow rate of 15 ml/min using the following gradient: (1) 5 CV of the starting buffer; (2) 0-1 M sodium chloride over 20 CV; (3) 1 M sodium chloride for 5 CV. The eluate was monitored for absorbance (280 nm). Active fractions from the HQ column were concentrated and desalted using a 10 kDa molecular weight limit membrane and subjected to a Bio-RP C4 reverse phase column (4.6×100 mm, Covance, Princeton, N.J.) and eluted at a flow rate of 4 ml/min using the following gradient: (1) 10 CV of the starting buffer of 5% acetonitrile in $H_2O$; (2) 5-95% acetonitrile in $H_2O$ over 2.5 CV; (3) 95% acetonitrile in $H_2O$ for 5 CV. The eluate was monitored for absorbance (280 nm), and the active fraction was pooled, lyophilized, and resuspended in phosphate-buffered saline (PBS), pH 7.4. The protein solution was injected onto a G3000PW gel permeation column (21.5×600 mm, TosoHaas, Montgomeryville, Pa.) and eluted with PBS, pH 7.4, at a flow rate of 5 ml/min.

Molecular mass and purity (>99%) of griffithsin were confirmed by Electrospray ionization mass spectrometry (ESI-MS), and the protein concentrations were determined by amino acid analysis. Native molecular weight was determined by calibrating standard proteins (albumin (68 kDa), cytochrome c (12.5 kDa), and aprotinin (6.5 kDa)) by their retention time (as measured by absorbance at 280 nm) and comparing the resulting calibration curve to the retention time of the active protein. Amino acid analysis was accomplished using a Beckman Model 6300 Automated Amino Acid Analyzer according to manufacturer protocols. N-terminal amino acid sequencing was performed using an Applied Biosystems Model 4774A Sequencer according to manufacturer protocols. Matrix-assisted laser desorption ionization-time of flight mass spectroscopy (MALDI-TOF MS) was performed using a Kratos Kompact Maldi III instrument (Shimadzu, Columbia, Md.) operated in a linear mode using sinapinic acid as a matrix and trypsin as an external standard. ESI-MS was performed with a JEOL SX102 equipped with an Analytica electrospray source. The spectrometer was calibrated using a lysozyme standard (molecular weight=14305.2) prior to each analysis. Samples were injected into the source in a 1:1 solution of hexafluorosopropanol and 2% acetic acid. The masses reported were averages calculated from the various charged states observed.

Griffithsin was subjected to digestion with cyanogen bromide (CNBr) and a variety of endoproteinases (Lys-C, Arg-C, and Asp-N) per manufacturer's instructions. The cleaved peptide products were purified by reversed-phase HPLC using a gradient of 0.05% aqueous trifluoroacetic acid for 20 min, then increasing to 60% acetonitrile in 0.05% aqueous trifluoroacetic acid over 100 min. Amino acid sequences were determined by sequential Edman degradation using an Applied Biosystems Model 494 sequencer according to the protocols of the manufacturer, and the masses of cleaved peptides were analyzed by MALDI-TOF mass spectrometer. The amino acid sequence of the native griffithsin polypeptide is set forth as SEQ ID NO:3.

In summary, the preliminary analysis of the crude aqueous extract of algae *Griffithsia* sp. in the NCI's primary in vitro anti-HIV screening assay (Weislow et al., supra) identified a protein that bound soluble gp120. The process described herein is illustrated in FIG. 1. Anti-HIV bioassay-guided fractionation of the aqueous resulted in the isolation of griffithsin. The aqueous extract was subjected to ammonium sulfate precipitation, hydrophobic interaction chromatography, anion exchange chromatography, reversed-phase chromatography, and size exclusion chromatography to produce a homogeneous protein fraction. SDS-PAGE analysis showed a single protein band with a relative molecular mass of approximately 13 kDa, named griffithsin. Purified griffithsin exhibited a single band by immunoblotting with anti-griffithsin polyclonal antibodies. The amino acid sequence of the purified griffithsin was established by N-terminal Edman degradation of the intact protein and by N-terminal sequencing of peptide fragments cleaved by CNBr and a variety of endopeptidases (Lys-C, Arg-C, and Asp-N) followed by reversed phase purification and MALDI-TOF mass spectrometric analysis. The entire 121 amino acid sequence was established except for a single amino acid at position 31, which does not match any of the common amino acids. Electrospray ionization mass spectrometric analysis of isolated griffithsin showed a molecular ion with m/z 12,770.05, and the calculated value for the deduced amino acid sequence without amino acid at position 31 was m/z 12619.00. It was deduced that the molecular mass of the amino acid at position 31 was 151.05. The amino acid analysis of griffithsin also agreed with the deduced primary sequence. These data fully support the proposed primary amino acid sequence of griffithsin. A search of the BLAST database (Altschul et al., *Nucleic Acids Res,* 25 (17), 3389-3402 (1997)) for identification of protein sequence similarities did not reveal any homologies of greater than eight contiguous amino acids nor >30% total sequence homology between griffithsin and any amino acid sequences of known proteins or transcription products of known nucleotide sequences, including the anti-HIV proteins cyanovirin-N and scytovirin.

Example 2

Figure 2:
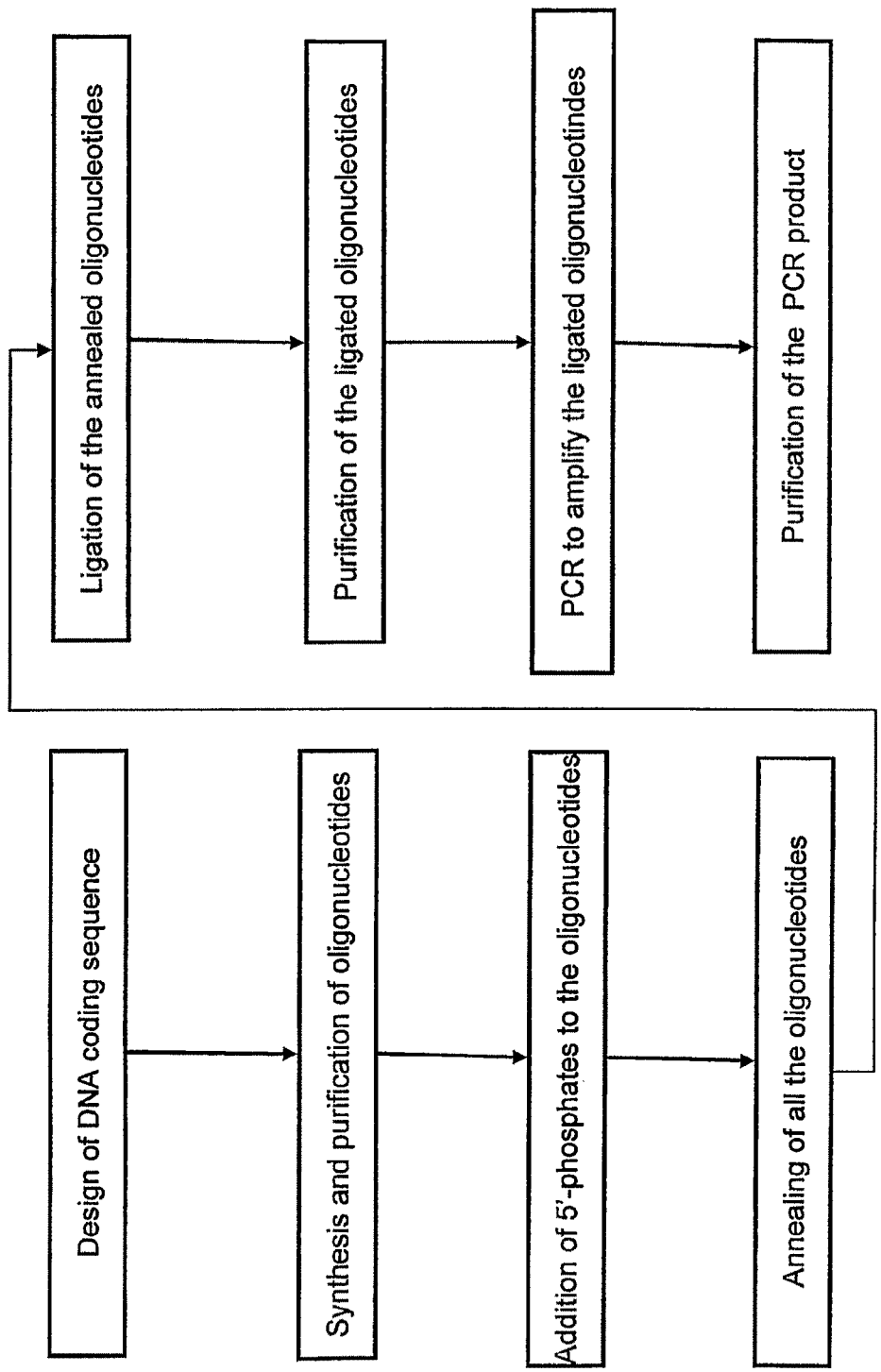

This example demonstrates the synthesis of griffithsin genes. The methods described herein are illustrated in FIG. 2.

The chemically deduced amino acid sequence of griffithsin was back-translated to elucidate the corresponding DNA coding sequence. Since amino acid residue 31 of native griffithsin did not appear to be one of the twenty common amino acids, alanine was substituted in this position (SEQ ID NO:2). In order to facilitate initial production and purification of recombinant griffithsin, a commercial expression vector pET-26b (+), from Novagen, Inc., Madison, Wis., for which reagents were available for affinity purification and detection, was selected. Appropriate restriction sites for ligation to pET-26b (+), and a stop codon, were included in the DNA sequence. SEQ ID NO:1 is an example of a DNA sequence encoding a synthetic griffithsin gene. A flowchart illustrating a method of synthesizing of a griffithsin gene is shown in FIG. 2.

A griffithsin-encoding DNA sequence was synthesized as 13 overlapping, complementary oligonucleotides and assembled to form the double-stranded coding sequence. Oligonucleotide elements of the synthetic DNA coding sequence were synthesized using a nucleic acid synthesizer (model 394, Applied Biosystems Inc., Foster City, Calif.). The purified 13 oligonucleotides were individually treated with T4 polynucleotide kinase, and 1 nM quantities of each were pooled and boiled for 10 minutes to ensure denaturation. The temperature of the mixture was then reduced to 70° C. for annealing of the complementary strands for 15 minutes, and further reduced to 60° C. for 15 minutes. The reaction was cooled on ice and T4 DNA ligase (2,000 units) additional ligase buffer was added to the reaction. Ligation of the oligonucleotides was performed with T4 DNA ligase overnight at 16° C. The resulting DNA was recovered and purified from the reaction buffer by phenol:chloroform extraction, ethanol precipitation, and further washing with ethanol.

The purified, double-stranded synthetic DNA was then used as a template in a polymerase chain reaction (PCR). One µl of the DNA solution obtained after purification of the ligation reaction mixture was used as a template. Thermal cycling was performed using a Perkin-Elmer instrument. "Pfu" thermostable DNA polymerase, restriction enzymes, T4 DNA ligase, and polynucleotide kinase were obtained from Stratagene, La Jolla, Calif. Pfu polymerase was selected for this application because of its claimed superiority in fidelity compared to the usual Taq enzyme. The PCR reaction product was run on a 2% agarose gel in TAE buffer. The 465 base pair DNA construct was cut from the gel and purified. The purified DNA, which was digested with Nde I and Xho I restriction enzymes, was then ligated into the multicloning site of the pet-26b(+) vector.

*E. coli* were transfected with the generated pET-26b(+)-construct, and recombinant clones were identified by analysis of restriction digests of plasmid DNA. Sequence analysis of one of these selected clones indicated that three bases deviated from the intended coding sequence. These "mutations," which presumably arose during the PCR amplification of the synthetic template, were corrected by a site-directed mutagenesis kit from Stratagene, La Jolla, Calif. The repair was confirmed by DNA sequence analysis.

For preparation of a DNA sequence encoding a griffithsin polypeptide tagged with a penta-His peptide at the C-terminal end of griffithsin (e.g., SEQ ID NO:4), the aforementioned recombinant griffithsin construct was subjected to site-directed mutagenesis to eliminate stop codons located between the griffithsin coding sequence and the penta-His peptide coding sequence using a site-directed mutagenesis kit from Stratagene, La Jolla, Calif. A pair of mutagenic oligonucleotide primers were synthesized, which included portions of the codons encoding the griffithsin polypeptide and penta-His peptide, but lacked the stop codons. Annealing of these mutagenic primers with the template DNA and extension by DNA polymerase resulted in the generation of a DNA construct encoding a fusion protein comprising the griffithsin amino acid sequence linked to a penta-His peptide tag. DNA sequencing verified the presence of the intended sequence.

Example 3

This example demonstrates the expression of an N-terminal His-tagged-griffithsin gene.

A recombinant griffithsin protein and a C-terminal, His-tagged griffithsin protein encoded by the nucleic acids of Example 2 did not efficiently translocate to the periplasmic fraction of *E. coli* following protein expression. In addition, the majority of the produced proteins accumulated in the inclusion bodies of *E. coli* without the cleavage of a pelB signal sequence located at the N-terminus of the griffithsin protein. Thus, steps were taken to express griffithsin in the cytosolic fraction of *E. coli*.

The pET-26b(+)-griffithsin DNA construct was used as a template PCR using a pair of appropriate primers. The PCR product was designed to have a "penta-His" peptide and thrombin recognition site at the N-terminal end of the griffithsin polypeptide, providing for production of a N-terminal, His-tagged-griffithsin fusion protein. The PCR reaction product was purified from an agarose gel. The purified DNA, which was digested with Nco I and Xho I restriction enzymes, was ligated into the expression vector pET-28a(+) vector (Novagen, Inc., Madison, Wis.).

Figure 3:
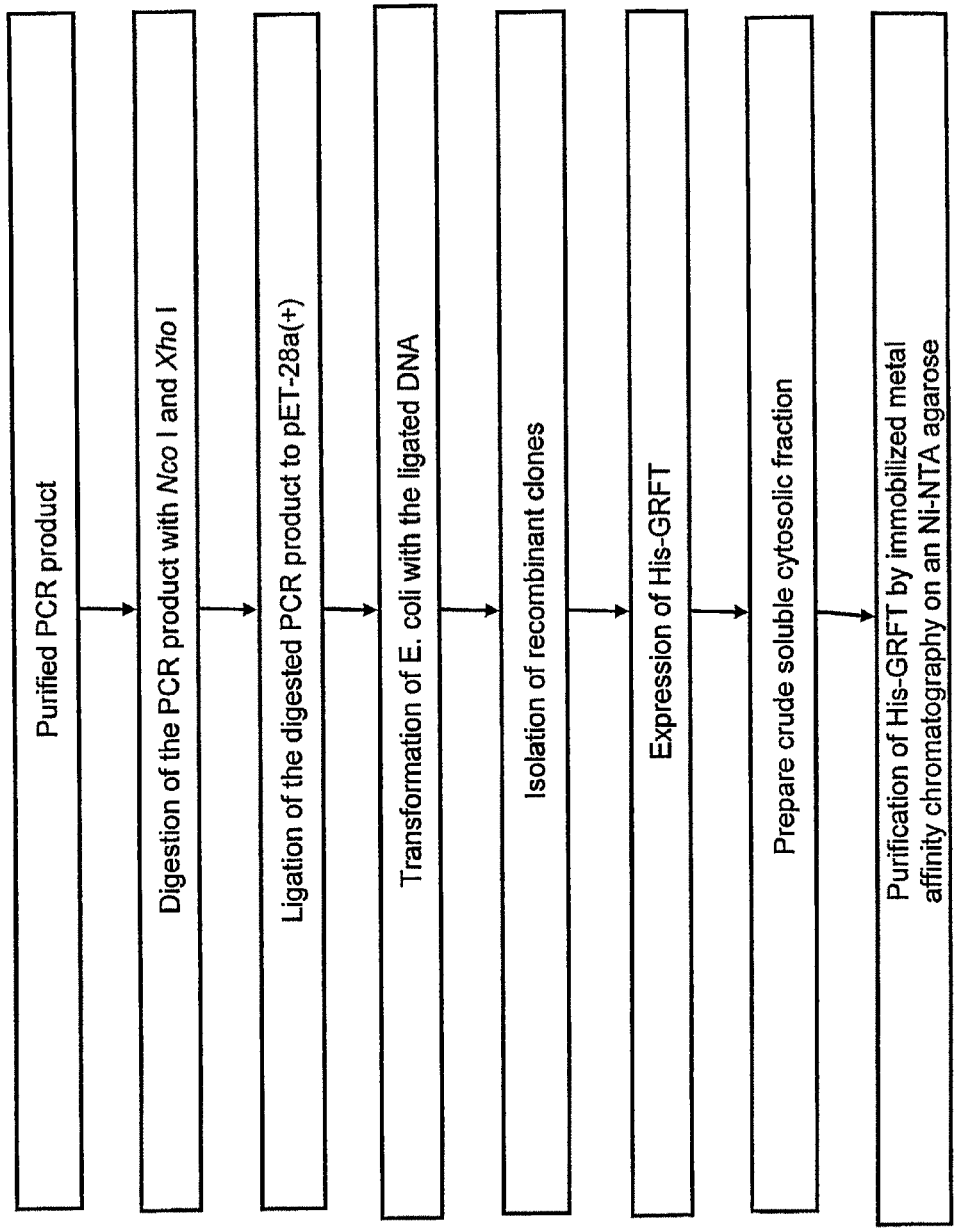

*E. coli* (strain BL21 (DE3)) were transfected with the pET-28a(+) vector containing the nucleic acid coding sequence for the His-tagged-griffithsin fusion protein (see SEQ ID NO:4). Selected clones were seeded into small-scale shake flasks containing LB growth medium with 30 μg/ml kanamycin and expanded by incubation at 37° C. Larger-scale Erlenmeyer flasks (0.5-3.0 liters) were then seeded. The culture was allowed to grow to a density of 0.5-0.7 $OD_{600}$ units. The expression of the His-tagged-griffithsin fusion protein was induced by adding IPTG to a final concentration of 1 mM and continuing incubation at 37° C. for 3-6 hrs. Bacteria were harvested by centrifugation, and the soluble fraction was obtained using BugBuster™ reagent and Benzonase nuclease (Novagen, Inc., Madison, Wis.). Crude soluble fractions showed both anti-HIV activity and presence of a His-tagged-griffithsin fusion protein by Western-blotting. In addition, the His-tagged-griffithsin protein accumulated in the inclusion bodies of *E. coli*. A flowchart illustrating a method of expressing and purifying recombinant His-tagged-griffithsin is shown in FIG. 3.

The purity (~98%) of recombinant His-tagged griffithsin was confirmed by SDS-PAGE on 16% Tricine gel stained by Coomassie Blue staining. The protein showed the expected molecular mass for griffithsin (i.e., 14.6 kDa). Protein concentrations were determined based on extinction coefficient at 280 nm of the protein. Approximately 1.6 mg of recombinant His-tagged griffithsin was purified from 1 L of *E. coli* culture. The purified protein demonstrated gp120-binding and anti-viral activity equivalent to that of native griffithsin.

This example illustrates a method of producing recombinant griffithsin, which displays physical and functional properties similar, if not identical, to that of natural griffithsin.

Example 4

This example describes a method of purifying a recombinant His-tagged-griffithsin protein.

Using an immobilized metal affinity chromatography set-up including Ni-NTA agarose (QIAGEN Inc., Valencia, Calif.), a His-tagged-griffithsin fusion protein (as described in Example 3) was purified.

The soluble fraction described in Example 3 was loaded onto 20 ml gravity columns containing affinity matrix. The columns were washed extensively with washing buffer (50 mM $NaH_2PO_4$, 300 mM NaCl, 20 mM imidazole, pH 8.0) to remove contaminating proteins. Since His-tagged griffithsin cannot compete for binding sites on the Ni-NTA resin if the imidazole concentration is increased to 100-250 mM, the His-tagged griffithsin protein was eluted by applying elution buffer (50 mM $NaH_2PO_4$, 300 mM NaCl, 250 mM imidazole, pH 8.0) through the column. Column fractions and wash volumes were monitored by Western-blot analysis using Penta-His™ antibody (QIAGEN Inc., Valencia, Calif.) or anti-griffithsin antibody. Fractions containing the purified His-tagged griffithsin protein were pooled, dialyzed extensively against distilled water, and lyophilized.

Potent cytoprotective and anti-replicative activities of both natural and His-tagged recombinant griffithsin were observed using the HIV-1RF strain of HIB in CEM-SS cells. Both the natural and recombinant griffithsin polypeptides demonstrated a concentration-dependent inhibition of virus-induced cell killing. Griffithsin treatment also resulted in concomitant decreases in supernatant reverse transcriptase and viral core antigen, p24. Mid-to-high picomolar concentrations of griffithsin exhibited comparably potent activity against all of the representative T-tropic laboratory strains and primary isolates as well as M-tropic primary isolates. In the antiviral assays, there was little or no evidence of direct cytotoxicity of griffithsin to the uninfected control cells at the highest tested concentrations of griffithsin (78.3 to 783 nM). Griffithsin-pretreated uninfected CEM-SS cells retained normal susceptibility to HIV infection after the removal of griffithsin. In contrast, infectivity of cell-free virus was abolished after pretreatment and removal of griffithsin. These results indicate that griffithsin is a virucide. Cocultivation of uninfected and chronically infected CEM-SS with griffithsin resulted in concentration-dependent inhibition of cell-cell fusion. Additional binding and fusion inhibition assay using β-gal indicator cells showed similar results. Griffithsin inhibited fusion of CD4 β-gal cells with HL ⅔ cells and also inhibited cell-free HIV-1IIIB fusion and infection of β-gal cells in a concentration-dependent manner.

Example 5

This example illustrates the anti-HIV activity of natural griffithsin polypeptide and His-tagged griffithsin polypeptide.

Pure proteins were initially evaluated for antiviral activity using an XTT-tetrazolium anti-HIV assay described previously (Boyd, in *Aids, Etiology, Diagnosis, Treatment And Prevention* (1988), supra; Gustafson et al., *J. Med. Chem.*, 35: 1978-1986 (1992); Weislow (1989), supra; Gulakowski (1991), supra). A CEM-SS human lymphocytic target cell line was used in all assays maintained in RPMI 1650 medium (Gibco, Grand Island, N.Y.), without phenol red, supplemented with 5% fetal bovine serum, 2 mM L-Glutamine, and 50 mg/ml Gentamicin (complete medium).

Exponentially growing cells were pelleted and resuspended at a concentration of $2.0 \times 10^5$ cells/ml in complete medium. The Haitian variant of HIV, $HTLV-III_{RF}$ ($3.54 \times 10^6$ SFU/ml), was used throughout. Frozen virus stock solutions were thawed immediately before use and resuspended in complete medium to yield $1.2 \times 10^5$ SFU/ml. The appropriate amounts of the pure proteins for anti-HIV evaluations were dissolved in $H_2O$-DMSO (3:1), then diluted in complete medium to the desired initial concentration. All serial drug dilutions, reagent additions, and plate-to-plate transfers were carried out with an automated Biomek 1000 Workstation (Beckman Instruments, Palo Alto, Calif.).

Figure 4A:
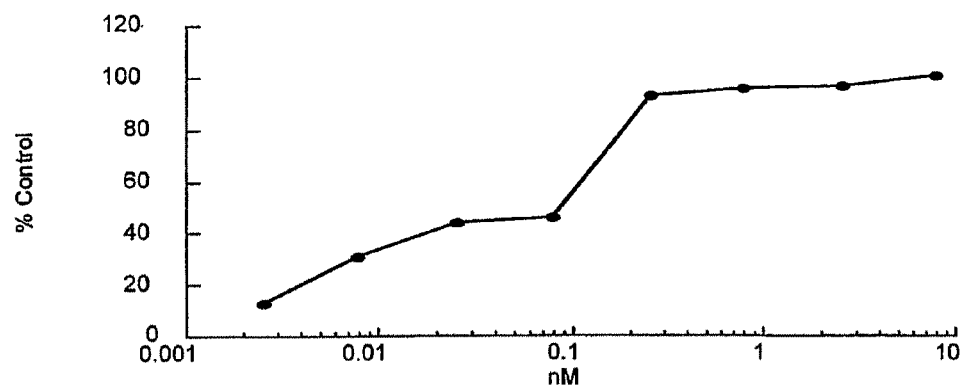
Figure 4B:
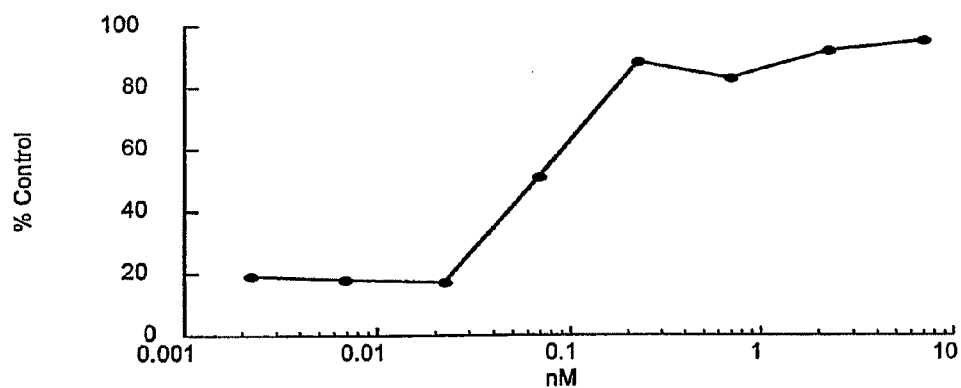
Figure 6:
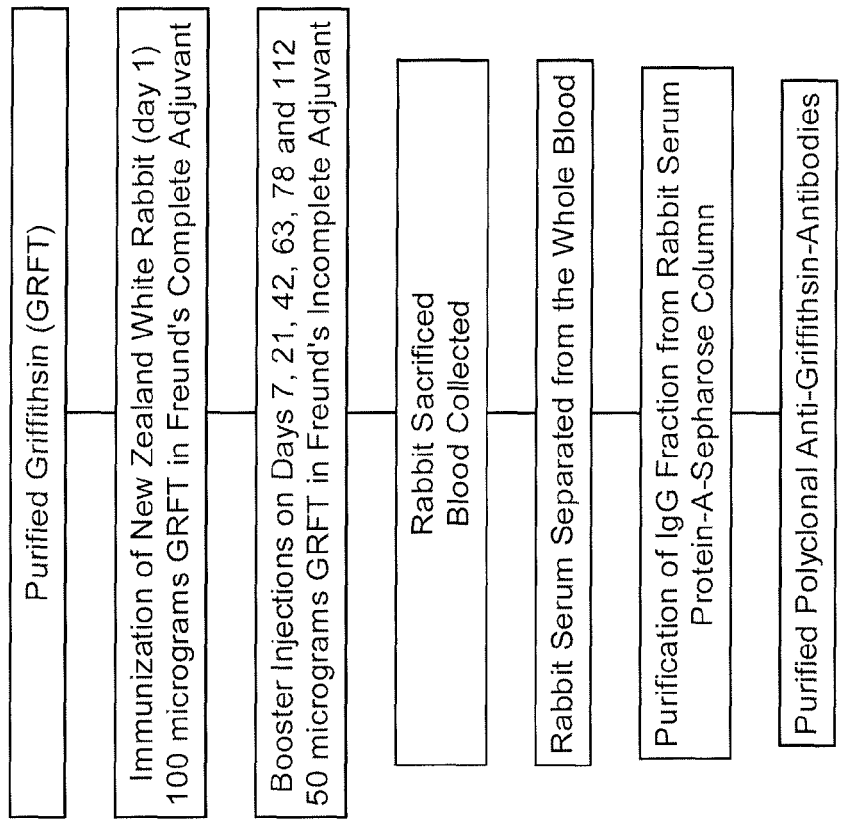

FIG. 4 summarizes the observed antiviral activities of native griffithsin from *Griffthsia* sp. (FIG. 4a) and recombinant His-tagged-fusion griffithsin (FIG. 4b). Effects of a range of concentrations of native griffithsin and HIS-tagged-griffithsin upon CEM-SS cells infected with HIV-1, as determined after 6 days in culture is illustrated in FIG. 6. Data points represent the percent of the respective uninfected, non-drug-treated control values. The two griffithsin polypeptides demonstrated potent anti-HIV activity with an $EC_{50}$ in the low nanomolar range and no significant evidence of direct cytotoxicity to the host cells at the highest tested concentrations (up to 1 mM).

Example 6

This example demonstrates that HIV viral envelope gp120 is the principal target for griffithsin.

To determine the affinity of griffithsin for a series of protein standards, 100 ng each of gp160, gp120, gp41, sCD4, bovine IgG, α-acid glycoprotein, and aprotinin were subjected to ELISA as previously described (Bokesch et al., *Biochemistry*, 42: 2578-2584 (2003)). Briefly, the protein standards were bound to a 96-well plate, which was rinsed with PBST (three times) and blocked with BSA. Between each step of the protocol, the plate was rinsed with PBST (three times). The protein standards were incubated with griffithsin (100 ng/well), followed by incubation with a 1:500 dilution of an anti-griffithsin rabbit polyclonal antibody preparation. Griffithsin bound to the protein standards was detected by adding goat-anti-rabbit antibodies conjugated to alkaline phosphatase (Roche Molecular Biochemicals, Indianapolis, Ind.). Upon addition of alkaline phosphatase substrate buffer, absorbance was measured at 405 nm for each well. Glycosylation-dependent binding of griffithsin to gp120 was examined using an ELISA as above, with glycosylated and nonglycosylated gp120 (HIV-1$_{SF2}$ gp120) added to the 96-well plate and incubated with serial dilutions of griffithsin.

Figure 5A:
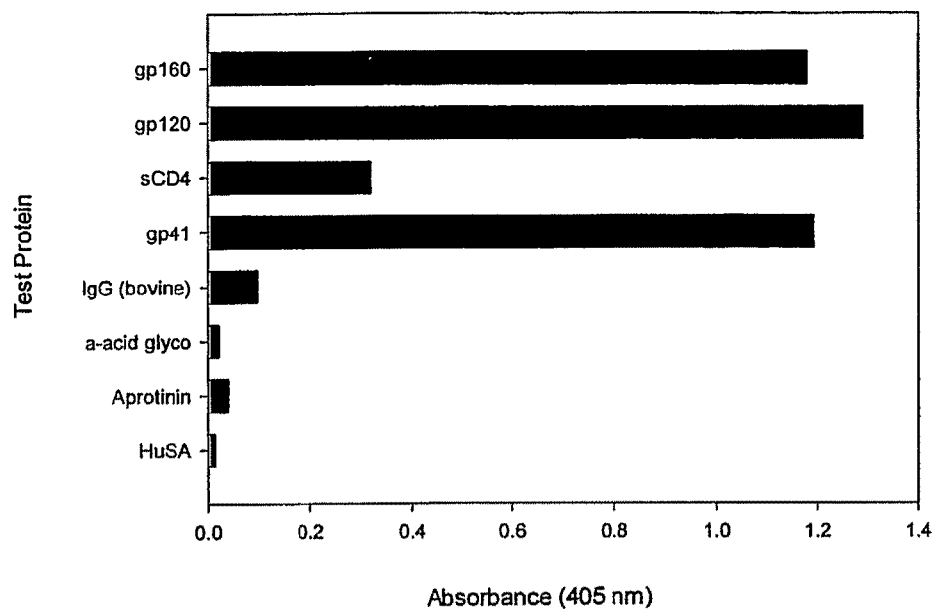
Figure 5B:
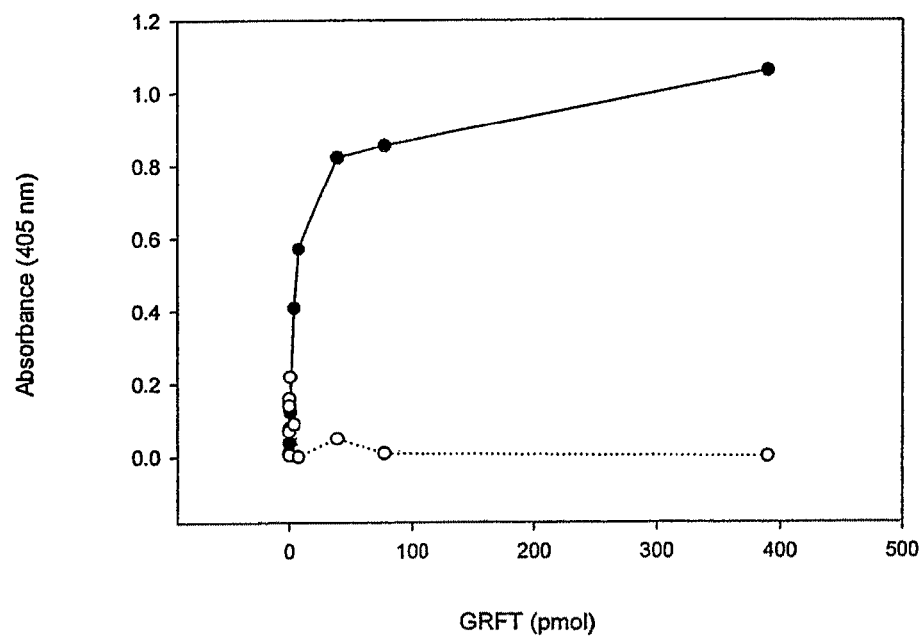

Griffithsin was tested for its ability to bind HIV envelope glycoproteins. Evidence for direct interaction of griffithsin with gp120, gp160, and to a lesser degree, gp41 was obtained from ELISA experiments (FIG. 5a). There was little or no detectable interaction between griffithsin and cCD4 or other reference proteins, including bovine IgG, α-acid glycoprotein, and aprotinin. An additional ELISA experiment showed that binding of griffithsin to sgp120 is both concentration-dependent and glycosylation-dependent (FIG. 5b).

To undertake preliminary mapping studies to define griffithsin-binding site on the gp120, we evaluated the effect of griffithsin on the reactivity of soluble CD4 (sCD4), cyanovirin-N, and a panel of monoclonal antibodies (mAb) with soluble gp120 (sgp120) in an ELISA format assay. These studies demonstrated that griffithsin interfered strongly with recognition of sgp120 by the mAbs 48d and 2G12. Griffithsin moderately interfered with sCD4 and mAb IgG1b12 binding to sgp120. Griffithsin had little or no effect on the recognition of sgp120 by mAbs that recognize the C1 region (or V3 loop), and the mAb 17b. However, additional studies demonstrated that pretreatment of sgp120 with sCD4 and the mAbs IgG 1b12, 48d, and 2G12 did not block subsequent binding of griffithsin to sgp120. Cyanovirin-N interfered strongly with the recognition of sgp120 by griffithsin. On the other hand, griffithsin pretreatment of sgp120 did not block subsequent binding of cyanovirin-N to sgp120.

Since griffithsin inhibited viral entry, we compared matched control and griffithsin-treated sgp120 preparations in a flow cytometric sgp120/CD4-expressing cell binding assay to determine whether griffithsin inhibits viral attachment or subsequent fusion events. The CEM-SS cell line expresses CD4, as demonstrated by the binding of target cells with both anti-Leu3a and anti-OKT4 monoclonal antibodies. After incubation of CEM-SS cells with sgp120, the cells were stained by anti-gp120 mAb-FITC. A concomitant decrease in the availability of the Leu3a epitope (i.e., the gp120-binding site on target cells) was observed. In other words, the sgp120 bound to the gp120 binding site on the target cells. As expected, little change in the staining specific for the OKT4 epitope (i.e., a non-gp120 binding site) was observed. These results are consistent with sgp120 binding of CD4 on the target cells. Pretreatment of sgp120 with griffithsin substantially recovered the availability of the Leu3a epitope, indicating that griffithsin completely blocked CD4-dependent sgp120 binding. However, overall sgp120 binding showed two peaks in the flow cytometry data when griffithsin-treated sgp120 was added to the cells. The decreased signal suggests inhibition of sgp120 binding to CD4 by griffithsin, which was consistent with the recovery of the availability of the Leu3a epitope. The increased signal suggests that the griffithsin/sgp120 complex also non-specifically bound to target cells.

This example demonstrates that griffithsin binds to a region of gp120 that recognizes CD4 on host cells.

Example 7

This example illustrates the broad-range anti-HIV activity of griffithsin.

Anti-viral assays used to study the activities of laboratory strains and primary isolates of virus have been previously published (Buckheit et al., *Antiviral Res.*, 21: 247-265 (1993)). The low passage HIV-1 pediatric isolate ROJO was derived as previously described (Buckheit et al., *AIDS Res. Hum. Retroviruses*, 10: 1497-1506 (1994)). Peripheral blood mononuclear cells (PBMC) and macrophages were isolated from hepatitis and HIV sero-negative donors following Ficoll-Hypaque centrifugation as described elsewhere (Gartner and Popovic, *Techniques in HIV Research*, Aldovini, A. and Walker, B., eds., Stockton Press, New York (1994) pp. 59-63). Mean $EC_{50}$ values were determined from concentration-response curves from eight dilutions of griffithsin (triplicate wells/concentration); assays for HIV-1 RF/CEM-SS employed XTT-tetrazolium; HIV-1 ROJO were tested in human PBMC cultures by supernatant reverse transcriptase activity; HIV-1 Ba-L and ADA were tested in human primary macrophage cultures by p24 ELISA assay. Standard errors averaged less than 10% of the respective means. The results of this study are summarized in Table 1 below.

TABLE 1

| Virus | Target Cell | Tropism | $EC_{50}$ (nM) |
| --- | --- | --- | --- |
| HIV-1 Laboratory Strain | | | |
| RF | CEM-SS | T | 0.043 |
| HIV Primary Isolates | | | |
| ROJO | PBMC | T | 0.63 |
| ADA | Macrophage | M | 0.50 |
| Ba-L | Macrophage | M | 0.098 |

The results show that griffithsin is potently active (sub-nanomolar $EC_{50}$ values) against a broad range of HIV isolates including T-tropic viruses (utilizing CCR5 as a co-receptor) and M-tropic viruses (utilizing CXCR4 as a co-receptor). This picomolar level of activity is more potent than that described for most of the current anti-HIV agents utilized in therapy or in development, including the entry inhibitors cyanovirin-N and Enfurtide®. The data also show that griffithsin is effective at inhibiting infection by both laboratory-adapted strains and, more importantly, primary clinical isolates of HIV (e.g., ROJO, ADA, and Ba-L). Finally, the results indicate that griffithsin is active regardless of the cell type used in the assay, having potent activity whether the cells were T-lymphocytes (CEM-SS), PBMCs, or macrophages. Griffithsin did not show any toxicity against any of the cell lines even at concentrations 1000-fold higher than the $EC_{50}$ values.

Example 8

This example describes the production of anti-griffithsin polyclonal antibodies. A flow diagram illustrating a method of producing anti-griffithsin antibodies is provided in FIG. 6.

A New Zealand white rabbit was immunized with 100 µg of griffithsin in Freund's complete adjuvant. Booster injections of 50 µg of griffithsin in Freund's incomplete adjuvant were administered on days 13, 29, 51, 64, 100, and 195. On days 7, 21, 42, 63, 78, and 112, 10 mL of blood was removed from the rabbit. On day 112 the rabbit was sacrificed and bled out. The IgG fraction of the immune sera of the rabbit was isolated by protein-A Sepharose affinity chromatography (Bio-Rad, Hercules, Calif.) according to the manufacturer's instructions. Reactivity of the polyclonal antibodies for griffithsin was demonstrated by immunoblot and ELISA studies with 1:500 to 1:3000 dilution of the rabbit immunoglobulin fractions.

For immunoblotting, samples were transferred to PVDF membranes following SDS-PAGE according to standard procedures. The membranes were incubated for 1 hour with anti-griffithsin polyclonal antibodies, washed three times with PBS containing 0.05% Tween 20 (PBST), and then treated with goat anti-rabbit IgG antibodies conjugated to horseradish peroxidase (Sigma, St. Louis, Mo.). After three washes with PBST, bound antibodies were visualized by incubating membranes in a solution of 0.05% 3,3'-diaminobenzidine and 0.003% $H_2O_2$.

The IgG fraction of rabbit polyclonal anti-griffithsin antibodies were purified after the final boost and animal sacrifice by using protein-A Sepharose chromatography on the 57 mL of rabbit serum collected. Following purification, 78 mL of purified anti-griffithsin IgGs were produced. The final concentration of protein was 335 micrograms/mL for a total yield of 27.3 mg of anti-griffithsin IgG. To analyze the specificity of the resulting antibody preparation, Western blot analysis was performed and resulted in the clear determination of specificity and avidity for griffithsin by the purified antibodies. A 1:250 dilution of the purified antibodies clearly visualized only the griffithsin from a mixture of griffithsin and other proteins. The response to griffithsin by the anti-griffithsin antibodies was also shown to be concentration-dependent.

Example 9

This example illustrates the anti-influenza virus activity of griffithsin.

All examined influenza viruses were passaged in Madin Darby canine kidney (MDCK) cells to prepare viral stocks. MDCK cells (from ATCC, Manassas, Va.) were grown in antibiotic-free minimum essential medium (MEM) with nonessential amino acids (Gibco, Long Island, N.Y.) containing 5% fetal bovine serum (FBS, HyClone Laboratories, Logan, Utah) and 0.1% NaHCO3. Test medium consisted of MEM with 0.18% NaHCO3, 10 units/mL trypsin, 1 µg of ethylenediaminetetraacetate (EDTA) per ml, and 50 µg gentamicin/mL.

Inhibition of virus-induced cytopathic effect (CPE) as determined by visual (microscopic) examination of infected cells and confirmed by increase in neutral red (NR) dye uptake into infected cells was used as an indicator of griffithsin antiviral activity. The CPE inhibition method was reported previously by Smee et al. (*Antiviral Res.*, 5: 251-259 (2001)). Seven concentrations of griffithsin were screened for antiviral activity against each virus in 96-well flat-bottomed microplates of cells. The griffithsin protein was added 5-10 minutes prior to addition of virus to the cells. The concentration of virus correspond to approximately 50% infection of cells in culture ($CCID_{50}$) per well. The virus challenge dose equals a multiplicity of infection of approximately 0.001 infectious particles per cell. The reaction proceeded at 37° C. for 72 hr. To perform the NR uptake assay for confirmation of antiviral activity, dye (0.34% concentration in medium) was added to the plates used to obtain visual scores of CPE. After 2 hours, color intensity of the dye absorbed by and subsequently eluted from the cells was determined by the method of Finter et al., *J. Gen. Virol.*, 5, 419-427 (1969) using a computerized EL-309 microplate autoreader (Bio-Tek Instruments, Winooski, Vt.). Antiviral activity was expressed as the 50% effective (virus-inhibitory) concentration ($EC_{50}$ value) determined by plotting griffithsin concentration versus percent inhibition on semi-logarithmic graph paper. Cytotoxicity of compounds was assessed in parallel with the antiviral determinations in the same microplates, except in the absence of virus. From these, 50% cytotoxic endpoints ($IC_{50}$ values) were determined. The results of this study are summarized in Table 2.

TABLE 2

| Influenza Virus Strain | $EC_{50}$ (µg/ml) |
| --- | --- |
| Beijing/262/95 (H1N1) | 0.07 |
| Texas/36/91 (H1N1) | 0.06 |
| Los Angeles/2/87 (H3N2) | 0.037 |
| Panama/2007/99 (H3N2) | 0.006 |
| Shandong/09/93 (H3N2) | 0.018 |
| Sydney/5/97 (H3N2) | 0.016 |
| Washington/05/96 (H3N2) | 0.016 |

Similar to the results with HIV, griffithsin was found to be potently active against a wide spectrum of influenza A viruses. These viruses included both H1N1 strains and H3N2 strains of influenza, which is especially significant in light of the fact that the highly virulent Fijian strain of influenza A that afflicted the United States in 2003/2004 was also a H3N2 strain. Griffithsin was not found to be toxic to the MDCK cell line utilized for these experiments, even when the cells were exposed to a high dose of griffithsin (10 micrograms/mL).

Example 10

This example describes a method of producing recombinant griffithsin.

Recombinant expression of His-tagged griffithsin in *E. coli* was optimized using a fermenter in combination with an auto-induction media. A seed culture was grown in LB media containing 30 µg/ml kanamycin in a shaker flask at 37° C. and 150 rpm for 17 hours. In addition, a fermenter containing an auto-induction media was inoculated with the seed culture. The ratio of auto-induction media to seed culture was approximately 50:1. The culture was grown at 37° C. for 24 hours. The final culture density was approximately 8.6 $OD_{600}$ units. The final culture was harvested by centrifugation, and the soluble fraction was obtained as described above.

Crude soluble fractions contained His-tagged-griffithsin fusion protein, which was detected by Western-blotting with anti-griffithsin polyclonal antibodies. The ratio of soluble: insoluble protein at approximately 15 kDa was 50:50. The ratio indicates that more griffithsin protein was produced in soluble fraction in this fermentation procedure compared with protein expression achieved using a shaker flask procedure. In addition, the fermentation procedure provided approximately 30-fold higher quantities of griffithsin protein than the shaker flask procedure. Approximately 50 mg of purified recombinant griffithsin was isolated from 1 L of the fermentation. The purified protein existed as a homodimer and demonstrated gp120 binding and anti-viral activity equivalent to that of native griffithsin.

The results of this example confirm a method of producing recombinant, anti-viral griffithsin protein.

The following references, to the extent that they provide exemplary procedural or other details supplementary to those set forth herein, are specifically incorporated herein by reference:

Birren et al., Cold Spring Harbor Laboratory Press, Cold Spring Harbor, N.Y. (1997), Birren et al., *Genome Analysis: A Laboratory Manual Series, Volume* 2, *Detecting Genes*, Cold Spring Harbor Laboratory Press, Cold Spring Harbor, N.Y. (1998), Birren et al., *Genome Analysis: A Laboratory Manual Series, Volume* 3, *Cloning Systems*, Cold Spring Harbor Laboratory Press, Cold Spring Harbor, N.Y. (1999), Birren et al., *Genome Analysis: A Laboratory Manual Series, Volume* 4, *Mapping Genomes*, Cold Spring Harbor Laboratory Press, Cold Spring Harbor, N.Y. (1999), Harlow et al., *Antibodies: A Laboratory Manual*, Cold Spring Harbor Laboratory Press, Cold Spring Harbor, N.Y. (1988), Harlow et al., *Using Antibodies: A Laboratory Manual*, Cold Spring Harbor Laboratory Press, Cold Spring Harbor, N.Y. (1999), and Sambrook et al., *Molecular Cloning: A Laboratory Manual*, 2nd edition, Cold Spring Harbor Laboratory Press, Cold Spring Harbor, N.Y. (1989).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

```
<160> NUMBER OF SEQ ID NOS: 5

<210> SEQ ID NO 1
<211> LENGTH: 363
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(363)

<400> SEQUENCE: 1 agc ctg acc cat cgc aag ttc ggt ggt agt ggt gga agt ccg ttc agc        48
Ser Leu Thr His Arg Lys Phe Gly Gly Ser Gly Gly Ser Pro Phe Ser
1               5                   10                  15 ggt ctg agc agc att gca gtt cgt agt ggc agc tat ctg gat gcg atc        96
Gly Leu Ser Ser Ile Ala Val Arg Ser Gly Ser Tyr Leu Asp Ala Ile
            20                  25                  30 atc att gat ggt gta cat cac ggt ggc tct ggt ggt aac ctg agt ccg       144
Ile Ile Asp Gly Val His His Gly Gly Ser Gly Gly Asn Leu Ser Pro
        35                  40                  45 acc ttc acc ttt gga tcc ggt gag tac atc agc aac atg acc att cgt       192
Thr Phe Thr Phe Gly Ser Gly Glu Tyr Ile Ser Asn Met Thr Ile Arg
    50                  55                  60 agt gga gac tac att gac aac atc agc ttt gaa acc aac atg ggt cgt       240
Ser Gly Asp Tyr Ile Asp Asn Ile Ser Phe Glu Thr Asn Met Gly Arg
65                  70                  75                  80 cgc ttt ggt ccg tat ggt gga tct ggt ggc agt gca aac acc ctg agc       288
Arg Phe Gly Pro Tyr Gly Gly Ser Gly Gly Ser Ala Asn Thr Leu Ser
                85                  90                  95
```

```
aac gtg aaa gtc atc cag atc aac ggt agt gca ggt gac tat ctg gat       336
Asn Val Lys Val Ile Gln Ile Asn Gly Ser Ala Gly Asp Tyr Leu Asp
            100                 105                 110 agc ctg gac atc tac tat gaa cag tac                                   363
Ser Leu Asp Ile Tyr Tyr Glu Gln Tyr
        115                 120

<210> SEQ ID NO 2
<211> LENGTH: 121
<212> TYPE: PRT
<213> ORGANISM: Artificial
<220> FEATURE:
<223> OTHER INFORMATION: Synthetic Construct

<400> SEQUENCE: 2

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Met Thr Ile Arg
    50                  55                  60

Ser Gly Asp Tyr Ile Asp Asn Ile Ser Phe Glu Thr Asn Met Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
        115                 120

<210> SEQ ID NO 3
<211> LENGTH: 121
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (31)..(31)
<223> OTHER INFORMATION: Xaa can be any naturally occurring amino acid

<400> SEQUENCE: 3

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Xaa Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Met Thr Ile Arg
    50                  55                  60

Ser Gly Asp Tyr Ile Asp Asn Ile Ser Phe Glu Thr Asn Met Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
        115                 120
```

<210> SEQ ID NO 4
<211> LENGTH: 417
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(417)

<400> SEQUENCE: 4

```
atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc ctg acc cat cgc aag ttc ggt ggt agt ggt gga agt ccg      96
Arg Gly Ser Leu Thr His Arg Lys Phe Gly Gly Ser Gly Gly Ser Pro
            20                  25                  30 ttc agc ggt ctg agc agc att gca gtt cgt agt ggc agc tat ctg gat     144
Phe Ser Gly Leu Ser Ser Ile Ala Val Arg Ser Gly Ser Tyr Leu Asp
        35                  40                  45 gcg atc atc att gat ggt gta cat cac ggt ggc tct ggt ggt aac ctg     192
Ala Ile Ile Ile Asp Gly Val His His Gly Gly Ser Gly Gly Asn Leu
    50                  55                  60 agt ccg acc ttc acc ttt gga tcc ggt gag tac atc agc aac atg acc     240
Ser Pro Thr Phe Thr Phe Gly Ser Gly Glu Tyr Ile Ser Asn Met Thr
65                  70                  75                  80 att cgt agt gga gac tac att gac aac atc agc ttt gaa acc aac atg     288
Ile Arg Ser Gly Asp Tyr Ile Asp Asn Ile Ser Phe Glu Thr Asn Met
                85                  90                  95 ggt cgt cgc ttt ggt ccg tat ggt gga tct ggt ggc agt gca aac acc     336
Gly Arg Arg Phe Gly Pro Tyr Gly Gly Ser Gly Gly Ser Ala Asn Thr
            100                 105                 110 ctg agc aac gtg aaa gtc atc cag atc aac ggt agt gca ggt gac tat     384
Leu Ser Asn Val Lys Val Ile Gln Ile Asn Gly Ser Ala Gly Asp Tyr
        115                 120                 125 ctg gat agc ctg gac atc tac tat gaa cag tac                         417
Leu Asp Ser Leu Asp Ile Tyr Tyr Glu Gln Tyr
    130                 135
```

<210> SEQ ID NO 5
<211> LENGTH: 139
<212> TYPE: PRT
<213> ORGANISM: Artificial
<220> FEATURE:
<223> OTHER INFORMATION: Synthetic Construct

<400> SEQUENCE: 5

```
Met Gly Ser Ser His His His His His His Ser Ser Gly Leu Val Pro
1               5                   10                  15

Arg Gly Ser Leu Thr His Arg Lys Phe Gly Gly Ser Gly Gly Ser Pro
            20                  25                  30

Phe Ser Gly Leu Ser Ser Ile Ala Val Arg Ser Gly Ser Tyr Leu Asp
        35                  40                  45

Ala Ile Ile Ile Asp Gly Val His His Gly Gly Ser Gly Gly Asn Leu
    50                  55                  60

Ser Pro Thr Phe Thr Phe Gly Ser Gly Glu Tyr Ile Ser Asn Met Thr
65                  70                  75                  80

Ile Arg Ser Gly Asp Tyr Ile Asp Asn Ile Ser Phe Glu Thr Asn Met
                85                  90                  95

Gly Arg Arg Phe Gly Pro Tyr Gly Gly Ser Gly Gly Ser Ala Asn Thr
            100                 105                 110
```

```
Leu Ser Asn Val Lys Val Ile Gln Ile Asn Gly Ser Ala Gly Asp Tyr
        115                 120                 125

Leu Asp Ser Leu Asp Ile Tyr Tyr Glu Gln Tyr
130                 135
```

What is claimed is:

1. A method of inhibiting a viral infection of a host, which method comprises administering to the host an effective amount of an anti-viral polypeptide or anti-viral polypeptide conjugate comprising SEQ ID NO:3 or a variant thereof, the variation consisting of rendering one or more of amino acid residues 45, 60, 71, or 104 of SEQ ID NO:3 glycosylation resistant, wherein the anti-viral polypeptide or anti-viral polypeptide conjugate has anti-viral activity, whereupon the viral infection is inhibited.

2. The method of claim 1, wherein the viral infection is an influenza viral infection.

3. The method of claim 2, wherein the anti-viral polypeptide or anti-viral polypeptide conjugate is administered topically to the host.

4. The method of claim 3, wherein the anti-viral polypeptide or anti-viral polypeptide conjugate is administered topically to the respiratory system.

5. The method of claim 4, wherein the anti-viral polypeptide or anti-viral polypeptide conjugate is administered as an aerosol or microparticulate powder.

6. The method of claim 1, wherein the viral infection is a retroviral infection.

7. The method of claim 6, wherein the retroviral infection is a human immunodeficiency viral infection.

8. A method of inhibiting a viral infection of a host, which method comprises administering to the host an effective amount of an anti-viral polypeptide or anti-viral polypeptide conjugate comprising SEQ ID NO:3, whereupon the viral infection is inhibited.

9. The method of claim 8, wherein the viral infection is an influenza viral infection.

10. The method of claim 9, wherein the anti-viral polypeptide or anti-viral polypeptide conjugate is administered topically to the host.

11. The method of claim 10, wherein the anti-viral polypeptide or anti-viral polypeptide conjugate is administered topically to the respiratory system.

12. The method of claim 11, wherein the anti-viral polypeptide or anti-viral polypeptide conjugate is administered as an aerosol or microparticulate powder.

13. The method of claim 8, wherein the viral infection is a retroviral infection.

14. The method of claim 13, wherein the retroviral infection is a human immunodeficiency viral infection.

15. A method of inhibiting a viral infection of a host, which method comprises administering to the host an effective amount of an anti-viral polypeptide or anti-viral polypeptide conjugate comprising SEQ ID NO:2, whereupon the viral infection is inhibited.

16. The method of claim 15, wherein the viral infection is an influenza viral infection.

17. The method of claim 16, wherein the anti-viral polypeptide or anti-viral polypeptide conjugate is administered topically to the host.

18. The method of claim 17, wherein the anti-viral polypeptide or anti-viral polypeptide conjugate is administered topically to the respiratory system.

19. The method of claim 18, wherein the anti-viral polypeptide or anti-viral polypeptide conjugate is administered as an aerosol or microparticulate powder.

20. The method of claim 15, wherein the viral infection is a retroviral infection.

21. The method of claim 20, wherein the retroviral infection is a human immunodeficiency viral infection.

* * * * *